US011875897B2

(12) United States Patent
Ichinose et al.

(10) Patent No.: US 11,875,897 B2
(45) Date of Patent: Jan. 16, 2024

(54) MEDICAL IMAGE PROCESSING APPARATUS, METHOD, AND PROGRAM, AND DIAGNOSIS SUPPORT APPARATUS, METHOD, AND PROGRAM

(71) Applicant: FUJIFILM Corporation, Tokyo (JP)

(72) Inventors: Akimichi Ichinose, Tokyo (JP); Keigo Nakamura, Tokyo (JP)

(73) Assignee: FUJIFILM Corporation, Tokyo (JP)

( * ) Notice: Subject to any disclaimer, the term of this patent is extended or adjusted under 35 U.S.C. 154(b) by 849 days.

(21) Appl. No.: 16/927,968

(22) Filed: Jul. 13, 2020

(65) Prior Publication Data

US 2020/0342990 A1    Oct. 29, 2020

Related U.S. Application Data

(63) Continuation of application No. PCT/JP2018/047853, filed on Dec. 26, 2018.

(30) Foreign Application Priority Data

Jan. 24, 2018  (JP) .................................. 2018-010014
Jul. 27, 2018  (JP) .................................. 2018-141697

(51) Int. Cl.
*G16H 50/20*     (2018.01)
*G16H 15/00*     (2018.01)
(Continued)

(52) U.S. Cl.
CPC ......... *G16H 50/20* (2018.01); *G06F 21/6245* (2013.01); *G06N 20/00* (2019.01);
(Continued)

(58) Field of Classification Search
CPC ........ G16H 50/20; G16H 15/00; G16H 30/20; G16H 30/40; G16H 50/70; G06F 21/6245;
(Continued)

(56) References Cited

U.S. PATENT DOCUMENTS

| 8,553,965 | B2 | 10/2013 | Zhao et al. |
| 10,007,985 | B2 * | 6/2018 | Leon ...................... A61B 6/032 |
| 2004/0078238 | A1 | 4/2004 | Thomas et al. |
| 2013/0208966 | A1 | 8/2013 | Zhao et al. |
| 2013/0223708 | A1 * | 8/2013 | Fukatsu ................ G06T 7/0012 382/128 |

(Continued)

FOREIGN PATENT DOCUMENTS

| JP | 2011125402 | 6/2011 |
| JP | 2013192624 | 9/2013 |

(Continued)

OTHER PUBLICATIONS

"Office Action of Japan Counterpart Application" with English translation thereof, dated Oct. 18, 2021, p. 1-p. 8.

(Continued)

*Primary Examiner* — Juan A Torres
(74) *Attorney, Agent, or Firm* — JCIPRNET

(57) ABSTRACT

Provided are a medical image processing apparatus, method, program, and a diagnosis support apparatus, method, and program that can efficiently collect medical images that have a large contribution to improving the accuracy of a diagnosis using medical images. The medical image processing apparatus includes a reception unit that receives an input of a medical image and patient information corresponding to the medical image, an analysis result acquisition unit that acquires an analysis result obtained by analyzing the medical image, a detection unit that detects whether or not the analysis result has been corrected, and a data processing unit that creates and stores data in which identification information capable of identifying a patient is concealed in a case where it is detected that the analysis result has been corrected.

14 Claims, 17 Drawing Sheets

(51) Int. Cl.
  *G16H 30/20* (2018.01)
  *G16H 50/70* (2018.01)
  *G16H 30/40* (2018.01)
  *G06N 20/00* (2019.01)
  *G06F 21/62* (2013.01)
  *G06T 7/00* (2017.01)

(52) U.S. Cl.
  CPC ............ *G06T 7/0012* (2013.01); *G16H 15/00* (2018.01); *G16H 30/20* (2018.01); *G16H 30/40* (2018.01); *G16H 50/70* (2018.01); *G06T 2207/20081* (2013.01)

(58) Field of Classification Search
  CPC .................. G06N 20/00; G06T 7/0012; G06T 2207/20081; G06T 2207/20084; G06T 2207/30004
  USPC .......................................................... 382/128
  See application file for complete search history.

(56) References Cited

U.S. PATENT DOCUMENTS

| | | | |
|---|---|---|---|
| 2013/0243244 A1 | 9/2013 | Miyamoto et al. | |
| 2015/0086133 A1* | 3/2015 | Grady | G06T 7/97 382/278 |

FOREIGN PATENT DOCUMENTS

| | | | |
|---|---|---|---|
| JP | 2014067229 | | 4/2014 |
| JP | 2014067229 A | * | 4/2014 |
| JP | 2015512100 | | 4/2015 |
| JP | 2017129922 | | 7/2017 |
| JP | 2017138991 | | 8/2017 |

OTHER PUBLICATIONS

Tada, Waichi., "AI Challengers Take on the World", with English concise explanation of relevance thereof, Nikkei Big Data.,Jan. 10, 2018, pp. 3-10.

Ohe, Kazuhiko., "New Trend of the establishment of medical image database infrastructure for Medical AI", Medical Informatics, Proceedings of the 37th Joint Conference on Medical Informatics(18th Conference of Japan Association for Medical Informatics)., Nov. 1, 2017, pp. 138-139.

"International Search Report (Form PCT/ISA/210) of PCT/JP2018/047853," dated Mar. 12, 2019, with English translation thereof, pp. 1-5.

"Written Opinion of the International Searching Authority (Form PCT/ISA/237) of PCT/JP2018/047853," dated Mar. 12, 2019, with English translation thereof, pp. 1-10.

* cited by examiner

MEDICAL IMAGE PROCESSING APPARATUS, METHOD, AND PROGRAM, AND DIAGNOSIS SUPPORT APPARATUS, METHOD, AND PROGRAM

CROSS-REFERENCE TO RELATED APPLICATIONS

The present application is a Continuation of PCT International Application No. PCT/JP2018/047853 filed on Dec. 26, 2018 claiming priorities under 35 U.S.C § 119(a) to Japanese Patent Application No. 2018-010014 filed on Jan. 24, 2018 and Japanese Patent Application No. 2018-141697 filed on Jul. 27, 2018. Each of the above applications is hereby expressly incorporated by reference, in its entirety, into the present application.

BACKGROUND OF THE INVENTION

1. Field of the Invention

The present invention relates to a medical image processing apparatus, method, program, and a diagnosis support apparatus, method, and program, and particularly relates to the medical image processing apparatus, method, and program, and the diagnosis support apparatus, method, and program for supporting a diagnosis using a medical image.

2. Description of the Related Art

In medical institutions, a patient may be diagnosed using medical images. In the diagnosis using medical images, an examination part of the patient is imaged, and a physician interprets medical images of the examination part to diagnose whether or not there is a lesion in the examination part.

JP2017-138991A discloses a cloud-based medical image processing system as a system for handling such medical images. In the medical image processing system disclosed in JP2017-138991A, a medical data store is provided in a cloud. The medical data store stores medical image data and medical data received from each data center via a network. Before transmitting the medical image data and the medical data from each data center to the cloud, personal information of a patient (patient name, address, social security number, credit card information, and the like) included in the medical data is anonymized by a data anonymizer comprised in a data gateway manager of each data center (paragraphs [0080] to [0083], FIG. 11).

SUMMARY OF THE INVENTION

Generally, a lesion included in medical images has various shapes, sizes, and types, and a single medical image may include a plurality of lesions. In a case where the size of the lesion is small, it is difficult to completely find the lesion included in medical images without omission. In addition, regarding a lesion having relatively few past cases (a rare disease or a rare case that is not a rare disease), it may be difficult for even a professional physician to find and diagnose the lesion. As described above, for a physician, interpreting and diagnosing medical images are an operation that is burdensome and takes a lot of time.

Further, in medical institutions, while a diagnosis using medical images has become widespread, generally, the number of professional physicians in charge of interpretation of medical images is small. For this reason, a small number of physicians interpret a large number of medical images, and the workload of each physician becomes excessive.

Therefore, in order to support a physician in making the diagnosis using medical images, it is conceivable to use machine learning (including deep learning and artificial intelligence (AI)). In a case where using the machine learning, in order to improve the accuracy of finding and diagnosing a lesion, it is necessary to collect and learn medical images of various shapes and types for each type of lesion.

However, in a case where an individual medical institution accumulates medical images acquired from patients, the medical image acquisition source is limited to patients at each medical institution. For this reason, it is difficult for each medical institution to collect medical images of various shapes and types for each type of lesion.

Therefore, in order to collect various medical images, it is also conceivable that a plurality of medical institutions collects medical images in cooperation. However, since the medical images may include personal information of a patient, sharing medical images between the plurality of medical institutions has a problem from the viewpoint of personal information protection.

JP2017-138991A relates to a technique for anonymizing personal information of a patient. According to the medical image processing system disclosed in JP2017-138991A, in a case of uploading medical image data and medical data from each data center, it is possible to anonymize the personal information of the patient included in the medical data. The medical image data and medical data are stored or archived in the medical data store in a cloud. According to the medical image processing system disclosed in JP2017-138991A, since the upload of the medical image data and the medical data in which the personal information of the patient has been anonymized can be accepted, it is possible to simultaneously protect the personal information of the patient and collect the medical image data from a plurality of data centers.

By the way, in order to perform the machine learning effectively and efficiently, it is preferable that learning is performed by collecting the medical images that greatly contribute to improving the accuracy of the diagnosis using medical images.

However, in general, the number of medical images related to atypical cases (for example, cases where interpretation and diagnosis are relatively difficult, such as rare diseases and rare cases) is smaller than the number of medical images related to typical cases (for example, cases where interpretation and diagnosis are relatively easy). Even in a case where learning is performed using the medical images related to the typical cases, the contribution to improving the accuracy of the machine learning is small with respect to the workload required for the learning.

According to the invention disclosed in JP2017-138991A, although the medical images related to the typical cases that make a small contribution to improving the accuracy of the diagnosis using the medical images are easier to gather, it has not been possible to efficiently collect the medical images that greatly contribute to improving the accuracy of the diagnosis using the medical images. For this reason, it has been difficult to effectively and efficiently perform machine learning using the medical images that greatly contributes to improving the accuracy of the diagnosis using the medical image.

The present invention has been made in view of such circumstances, and an object of the invention is to provide a medical image processing apparatus, method, program, and a diagnosis support apparatus, method, and program that can efficiently collect medical images that have a large contribution to improving the accuracy of a diagnosis using medical images.

In order to solve the above problems, a medical image processing apparatus according to a first aspect of the present invention comprises a reception unit that receives an input of a medical image and patient information corresponding to the medical image, an analysis result acquisition unit that acquires an analysis result obtained by analyzing the medical image, a detection unit that detects whether or not the analysis result has been corrected, and a data processing unit that creates and stores data in which identification information capable of identifying a patient is concealed in a case where it is detected that the analysis result has been corrected.

According to the first aspect, among analysis results by the analysis unit which is a medical image identification engine of medical institutions, data corrected by a physician, that is, data in which the analysis result by the analysis unit includes an error are subjected to perform concealment processing of patient identification information and are made available outside the medical institution where the medical image processing apparatus is installed. This makes it possible to efficiently collect the medical images that greatly contribute to improving the accuracy of the diagnosis using the medical images.

The medical image processing apparatus according to a second aspect of the present invention is, in the first aspect, an apparatus in which the detection unit detects that the analysis result has been corrected by comparing the analysis result with an input for the analysis result or a medical examination record of the patient.

The medical image processing apparatus according to a third aspect of the present invention is, in the first of second aspect, an apparatus in which, in the case where it is detected that the analysis result has been corrected, the data processing unit creates and stores data in which the identification information capable of identifying the patient is concealed on the basis of the medical image, the patient information, and the corrected analysis result.

The medical image processing apparatus according to a fourth aspect of the present invention is, in any one of the first to third aspects, an apparatus in which, in a case where the detection unit detects that an extraction result of a contour of a region included in the medical image has been corrected, the data processing unit creates and stores the data in which the identification information capable of identifying the patient is concealed on the basis of the medical image and the corrected contour.

The medical image processing apparatus according to a fifth aspect of the present invention is, in any one of the first to fourth aspects, an apparatus in which, in a case where the detection unit detects that a determination result of property of a region included in the medical image has been corrected, the data processing unit creates and stores the data in which the identification information capable of identifying the patient is concealed on the basis of the medical image and the corrected determination result.

The medical image processing apparatus according to a sixth aspect of the present invention is, in any one of the first to fifth aspects, an apparatus in which, in a case where the detection unit detects that an analysis result including one or more keywords or sentences obtained by an image analysis for the medical image has been corrected, the data processing unit creates and stores the data in which the identification information capable of identifying the patient is concealed on the basis of the medical image and the corrected analysis result including one or more keywords or sentences.

The medical image processing apparatus according to a seventh aspect of the present invention is, in any one of the first to sixth aspects, an apparatus in which the data processing unit records in advance a correspondence relationship between a type of the medical image or a type of analysis and a level of concealment of the identification information, and creates the data in which the identification information capable of identifying the patient is concealed on the basis of the correspondence relationship.

According to the seventh aspect, it is possible to perform appropriate concealment processing on the patient identification information by selecting a target of the concealment processing according to the type of the medical image and the type of analysis.

The medical image processing apparatus according to an eighth aspect of the present invention is, in any one of the first to seventh aspects, an apparatus in which, in a case where the medical image includes an image of a body surface of the patient, the data processing unit processes the medical image and conceals the image of the body surface.

According to the eighth aspect, it is possible to prevent the appearance and the like of the patient from being restored from the image of the body surface (body surface data) included in the medical image.

The medical image processing apparatus according to a ninth aspect of the present invention is, in any one of the first to eighth aspects, an apparatus in which, in the case where it is detected that the analysis result has been corrected, the data processing unit acquires a past medical image and patient information regarding the patient, and creates and stores data in which the identification information capable of identifying the patient is concealed, in the past medical image and patient information.

The medical image processing apparatus according to a tenth aspect of the present invention is, in any one of the first to ninth aspects, an apparatus in which the detection unit detects whether or not at least one of a plurality of analysis results at different time points regarding the patient has been corrected, and in which, in a case where it is detected that the analysis result at a first time point has been corrected, the data processing unit acquires a medical image and patient information at a second time point different from the first time point in addition to the medical image and the patient information at the first time point, and creates and stores data in which the identification information capable of identifying the patient is concealed, in the medical image and the patient information.

According to the ninth and tenth aspects, in a case where the analysis result of the medical image is corrected, it is possible to perform the concealment processing on a medical image of the same patient at another time point. This makes it possible to perform additional learning using analysis results of the medical image related to the same patient at multiple time points.

A diagnosis support apparatus according to an eleventh aspect of the present invention is a diagnosis support apparatus that presents information for supporting diagnosis and comprises a data acquisition unit that acquires a medical image of a patient to be diagnosed, an analysis unit that has performed learning using data created by the medical image processing apparatus in any one of the first to tenth aspects, and analyzes the medical image of the patient to be diagnosed, and a presentation unit that presents the analysis result.

According to the eleventh aspect, the data corrected by a physician among the analysis results by the medical image identification engine (the analysis unit) of medical institutions, that is, the data in which the analysis result by the medical image identification engine includes an error can be collected from the medical institutions and can be learned by the analysis unit.

A medical image processing method according to a twelfth aspect comprises, in a medical image processing apparatus, a reception step of receiving an input of a medical image and patient information corresponding to the medical image, an analysis result acquisition step of acquiring an analysis result obtained by analyzing the medical image, a detection step of detecting whether or not the analysis result has been corrected, and a data processing step of creating and storing data in which identification information capable of identifying a patient is concealed in a case where it is detected that the analysis result has been corrected.

A diagnosis support method according to a thirteenth aspect comprises a step of performing learning in the analysis unit for analyzing a medical image using data created by the medical image processing method according to the twelfth aspect, a step of acquiring a medical image of a patient to be diagnosed, a step of analyzing the medical image of the patient to be diagnosed by the analysis unit that has performed the learning, and a step of presenting an analysis result.

A medical image processing program according to a fourteenth aspect of the present invention causes a computer to realize a function of receiving an input of a medical image and patient information corresponding to the medical image, a function of acquiring an analysis result obtained by analyzing the medical image, a function of detecting whether or not the analysis result has been corrected, and a function of creating and storing data in which identification information capable of identifying a patient is concealed in a case where it is detected that the analysis result has been corrected.

A diagnosis support program according to a fifteenth aspect of the present invention causes a computer to realize a function of performing learning in an analysis unit for analyzing a medical image using data created by executing the medical image processing program according to the fourteenth aspect, a function of acquiring a medical image of a patient to be diagnosed, a function of analyzing the medical image of the patient to be diagnosed by the analysis unit that has performed the learning, and a function of presenting an analysis result.

According to the present invention, the data corrected by a physician among the analysis results by the medical image identification engine of medical institutions, that is, the data in which the analysis result by the medical image identification engine includes an error can be collected from the medical institutions. This makes it possible to efficiently collect the medical images that greatly contribute to improving the accuracy of the diagnosis using the medical images.

DESCRIPTION OF THE PREFERRED EMBODIMENTS

Hereinafter, embodiments of a medical image processing apparatus, method, and program, and a diagnosis support apparatus, method, and program according to the embodiment of the present invention will be described with reference to the accompanying drawings.

First Embodiment (Medical Support System)

Figure 1:
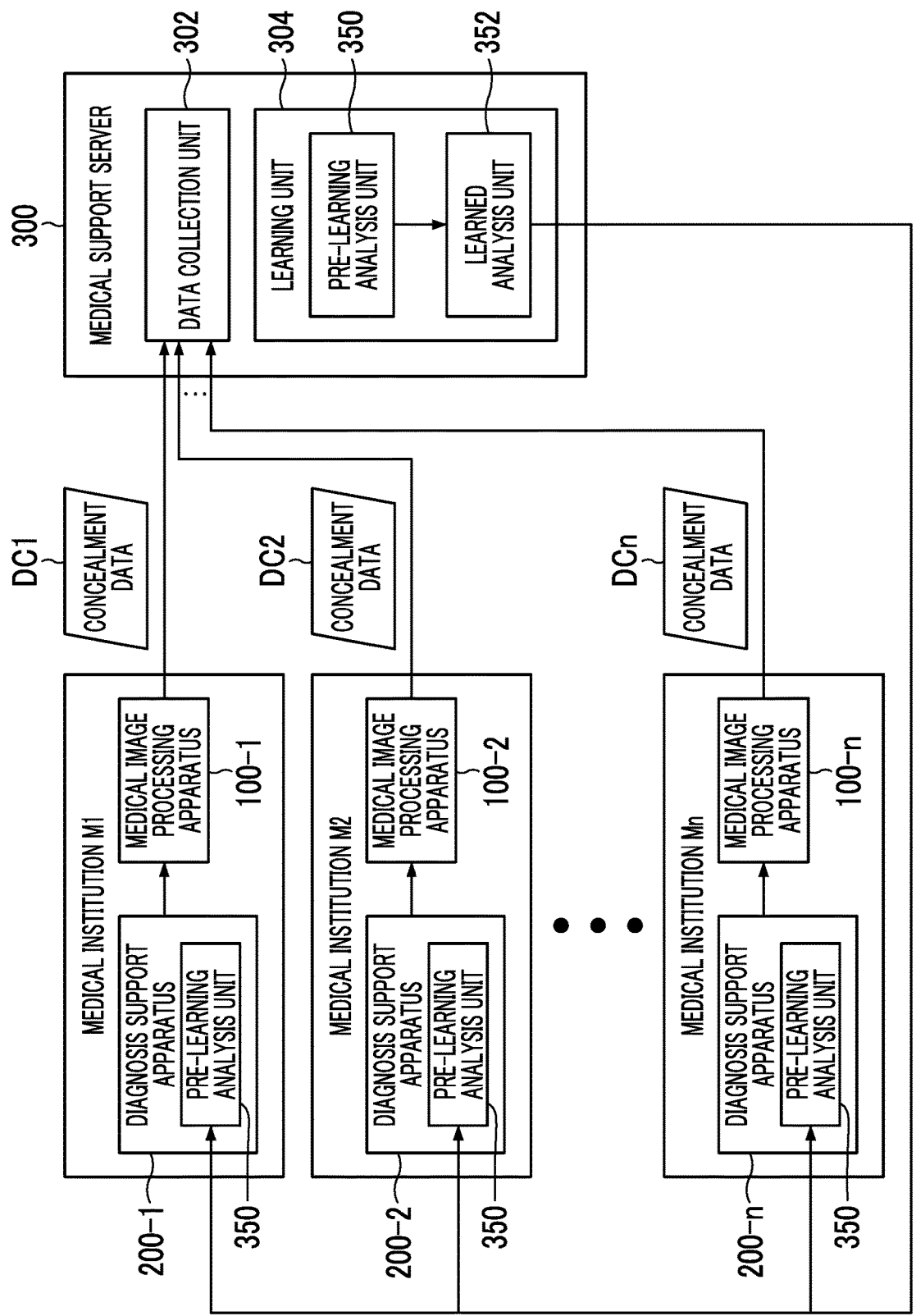
FIG. 1 is a block diagram illustrating a medical support system according to a first embodiment of the present invention.

First, an outline of the medical support system will be described with reference to FIG. 1. FIG. 1 is a block diagram illustrating a medical support system according to a first embodiment of the present invention.

In FIG. 1, medical institutions M1, M2, . . . , Mn are facilities that provide medical care to patients, and are, for example, hospitals, dental clinics, clinics, and the like.

As illustrated in FIG. 1, a medical support system 10 according to the present embodiment includes medical image processing apparatus 100-1, 100-2, . . . , 100-n, diagnosis support apparatus 200-1, 200-2, . . . , 200-n, and a medical support server 300 respectively installed in the medical institutions M1, M2, . . . , Mn. The medical support server 300 includes a data collection unit 302 and a learning unit 304.

the medical image processing apparatus 100-1, 100-2, . . . , 100-*n*, and the diagnosis support apparatus 200-1, 200-2, . . . , 200-*n* respectively installed in the medical institutions M1, M2, . . . , Mn can communicate with the medical support server 300 via a network (for example, internet or intranet). Here, the medical image processing apparatus 100-1, 100-2, . . . , 100-*n*, and the diagnosis support apparatus 200-1, 200-2, . . . , 200-*n*, and the medical support server 300 may be connected via a virtual private network (VPN), and can use an internet VPN using internet, or an internet protocol-VPN (IP-VPN) using a communication network (closed network) that is not open to the outside of an internet service provider, for example. In addition, the medical image processing apparatus 100-1, 100-2, . . . , 100-*n*, and the diagnosis support apparatus 200-1, 200-2, . . . , 200-*n*, and the medical support server 300 may be connected via a dedicated line.

The medical support server 300 may be installed in a place different from the medical institutions M1, M2, . . . , Mn (for example, a provider of a medical support service using the medical support server 300), or may be installed in one medical institution of the medical institutions M1, M2, . . . , Mn.

In the following description, the medical image processing apparatus 100-1, 100-2, . . . , 100-*n* of the medical institutions M1, M2, . . . , Mn, and the diagnosis support apparatus 200-1, 200-2, . . . , 200-*n* may be abbreviated as a medical image processing apparatus 100-*i* and a diagnosis support apparatus 200-*i* (i=1, 2, . . . , n) of a medical institution Mi.

In the medical support system 10 according to the present embodiment, each of diagnosis support apparatus 200-*i* includes a medical image identification engine (a pre-learning analysis unit 350) for analyzing medical images. The diagnosis support apparatus 200-*i* acquires a medical image (for example, an X-ray image) and patient information (for example, patient identification information, patient identification (ID), patient name, and the like) from an examination apparatus (reference numeral 150 in FIG. 2) installed in the medical institution Mi, and analyzes the medical image using the pre-learning analysis unit 350. The diagnosis support apparatus 200-*i* presents the diagnosis support information including the analysis result and the medical image to a physician, and receives an input such as approval or correction from the physician. Analysis result information including an analysis result input by the physician for approval or correction is transmitted to the medical image processing apparatus 100-*i* together with the medical image and the patient information.

The medical image processing apparatus 100-*i* performs concealment processing for concealing identification information that can identify a patient for the data in which correction has been input by the physician among the medical image, the patient information and the analysis result information, that is the data in which the analysis result by the medical image identification engine (the pre-learning analysis unit 350) includes an error to generate a concealment data DCi.

The medical support server 300 collects concealment data DC1, DC2, . . . , DCn respectively from the medical image processing apparatus 100-1, 100-2, . . . , 100-*n* of the medical institutions M1, M2, . . . , Mn by the data collection unit 302.

The learning unit 304 of the medical support server 300 includes a medical image identification engine (the pre-learning analysis unit 350) of the same version as the medical institution Mi. The pre-learning analysis unit 350 is a medical image identification engine before learning using the concealment data DC1, DC2, . . . , DCn, and a learned analysis unit 352 is a medical image identification engine after learning using the concealment data DC1, DC2, . . . , DCn. The learning unit 304 causes the pre-learning analysis unit 350 to perform learning using the concealment data DC1, DC2, . . . , DCn collected from the medical institutions M1, M2, . . . , Mn. The learned analysis unit 352 generated by the learning is transmitted respectively from the medical support server 300 to the diagnosis support apparatus 200-1, 200-2, . . . , 200-*n*.

The diagnosis support apparatus 200-1, 200-2, . . . , 200-*n* of the medical institutions M1, M2, . . . , Mn updates the medical image identification engine by acquiring the learned analysis unit 352 from the medical support server 300 and replacing it with the pre-learning analysis unit 350, respectively. Thus, the diagnosis support apparatus 200-1, 200-2, . . . , 200-*n* can analyze another medical image using the learned analysis unit 352, generate the diagnosis support information including the analysis result, and present it to the physician.

According to the present embodiment, the data corrected by the physician among the analysis results by the pre-learning analysis unit 350 of the medical institution Mi, that is, the data in which the analysis result by the pre-learning analysis unit 350 includes an error is collected, and the pre-learning analysis unit 350 is made to perform learning. This makes it possible to efficiently collect the medical images that greatly contribute to improving the accuracy of the diagnosis using the medical images.

The learning in the learning unit 304 and the update of the medical image identification engine may be performed periodically. In addition, the learning in the learning unit 304 and the update of the medical image identification engine may be performed according to the capacity of the concealment data DCi transmitted to and accumulated in the medical support server 300, for example, in a case where the number of accumulated medical images becomes equal to or more than a predetermined number. In addition, the execution timing of the learning in the learning unit 304 and the update of the medical image identification engine may be randomly set by an operator. Further, in a case where it is determined that the importance is high according to the importance of the correction of the analysis result (for example, the amount or type of the corrected information), the learning in the learning unit 304 and the update of the medical image identification engine may be executed.

Figure 2:
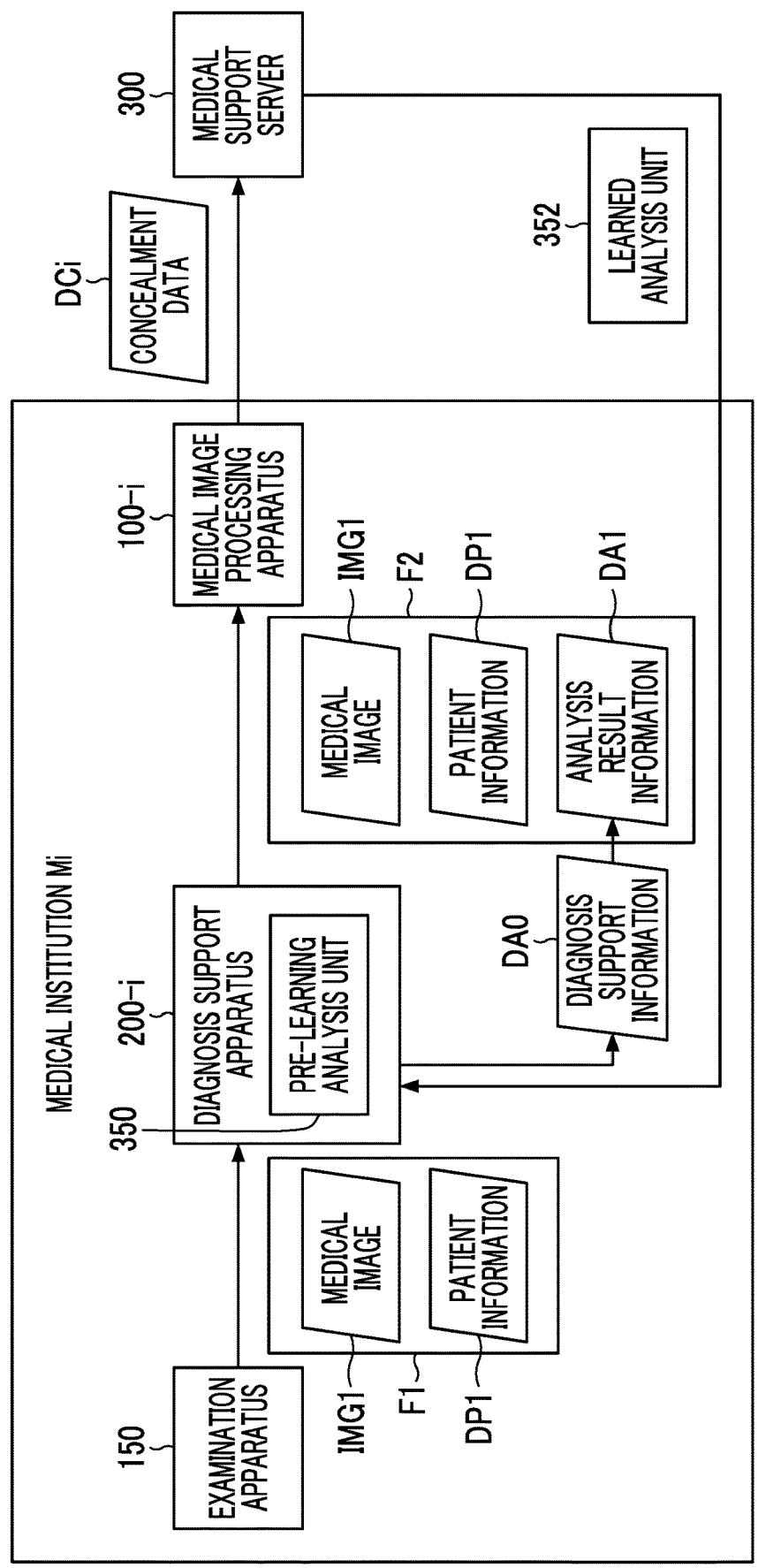
FIG. 2 is a block diagram for explaining a flow of processing in the medical support system according to the first embodiment of the present invention.
Figure 3:
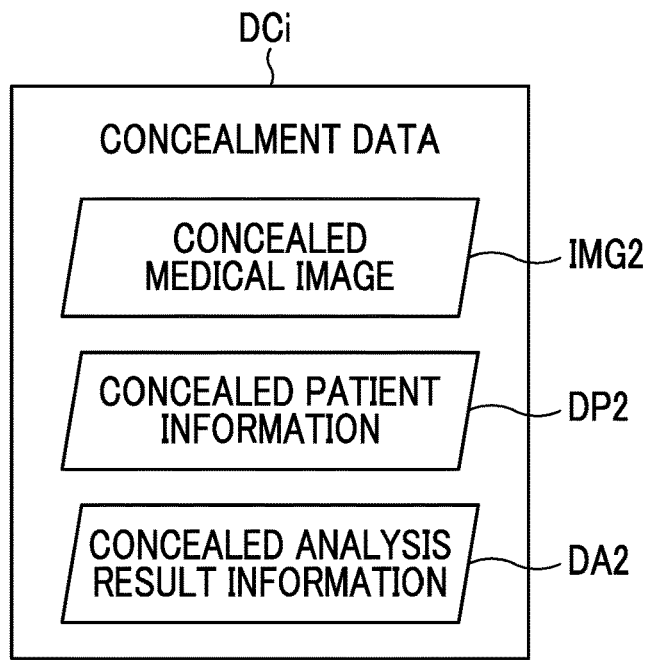
FIG. 3 is a data block diagram illustrating an example of concealment data.

Next, a flow of processing in the medical support system will be specifically described with reference to FIGS. 2 and 3. FIG. 2 is a block diagram for explaining a flow of processing in the medical support system according to the first embodiment of the present invention, and FIG. 3 is a data block diagram illustrating an example of the concealment data.

An examination apparatus 150 illustrated in FIG. 2 is an apparatus for imaging an examination part of a patient in the medical institution Mi, for example, an X-ray imaging apparatus, a computed tomography (CT), a positron emission tomography (PET), a single photon emission computed tomography (SPECT), a magnetic resonance imaging (MM), a mammography examination apparatus, or the like.

The examination apparatus 150 acquires a medical image IMG1 (for example, an X-ray image) by imaging the examination part of the patient. Further, the examination apparatus 150 comprises an input unit for receiving an input of patient information DP1 (for example, patient identification information, patient ID, patient name, and the like) regarding the patient. The input unit of the examination apparatus 150 may include a keyboard for inputting characters. In addition, the input unit of the examination apparatus 150 may include a reading apparatus (for example, a magnetic card reader, an integrated circuit (IC) card reader) that reads information on a registration card of the patient and a searching unit for acquiring the patient information DP1 from a hospital information systems (HIS) including a database in which information on patients of the medical institution Mi is housed using information on the registration card read by the reading apparatus.

The medical image IMG1 of the examination part of the patient and the patient information DP1 acquired by the examination apparatus 150 are transmitted to the diagnosis support apparatus 200-i. Here, the medical image IMG1 and the patient information DP1 can be created in a data format conforming to, for example, a digital imaging and communications in medicine (DICOM) or a medical image processing systems (MIPS) standard of Japan Medical Imaging and Radiological Systems Industries Association.

In the present embodiment, a file including the medical image IMG1 and the patient information DP1 transmitted from the examination apparatus 150 to the diagnosis support apparatus 200-i is referred to as a DICOM file F1. The patient information DP1 can be included in, for example, a tag or a private tag of the DICOM file F1. The private tag is a tag that can be independently defined by a modality maker (a maker of the examination apparatus 150 used for generating the medical image IMG1), and the like. The tag of the DICOM file will be described later (refer to tables 1 to 3).

The diagnosis support apparatus 200-i acquires the medical image IMG1 and the patient information DP1 of the examination part of the patient from the examination apparatus 150. The diagnosis support apparatus 200-i analyzes the medical image IMG1 of the examination part of the patient using the pre-learning analysis unit 350, and generates diagnosis support information DA0 including the analysis result. The diagnosis support information DA0 includes, for example, a result of region division of the examination part, an extraction result of a region and contour of the organ or bone included in the examination part, information such as whether or not the examination part includes a lesion, and in a case where a lesion is included, information such as the type of the lesion or a candidate for the type of lesion. The diagnosis support information DA0 is presented to the physician by a presentation unit (a display unit 210 or a physician terminal 220 in FIG. 10), and is used to assist the physician in making a diagnosis using the medical image IMG1.

The diagnosis support apparatus 200-i comprises an operation input unit (an operation unit 204 or the physician terminal 220 in FIG. 10) that receives an input of approval or correction, and an input of selection of a candidate for the type of lesion included in the diagnosis support information DA0 for the analysis result included in the diagnosis support information DA0. The physician can interpret the medical image IMG1 while referring to the diagnosis support information DA0 presented on the presentation unit, and can approve and correct the diagnosis support information DA0 using the operation input unit.

In the diagnosis support apparatus 200-i, the diagnosis support information DA0 that has been approved or corrected by the physician is referred to as analysis result information DA1. Additional information (for example, a flag) indicating whether or not the diagnosis support information DA0 has been approved or corrected by the physician is added to the analysis result information DA1. In a case of receiving the input of the correction from the operation unit 204 or the physician terminal 220, the diagnosis support apparatus 200-i (a controller 202 in FIG. 10) creates a DICOM file F2 by adding the analysis result information DA1 to the DICOM file F1. At this time, the analysis result information DA1 and the additional information (such as a flag indicating the presence or absence of correction) can be included in a tag or a private tag of the DICOM file F2. In addition, the analysis result information DA1 and the additional information (such as a flag indicating the presence or absence of correction) can be files different from the DICOM file F2. The diagnosis support apparatus 200-i transmits the DICOM file F2 to the medical image processing apparatus 100-i.

For example, in a case of medical images of regions of heart and lung, the regions and contours of the heart and lung are extracted by the medical image identification engine to measure a cardio-thoracic ratio. In a case where an error is found in a detection result of regions of the heart and lung as a result of image interpretation by a physician, the physician corrects a marker indicating the regions or the contours of the heart and lung in the diagnosis support apparatus 200-i. The controller 202 of the diagnosis support apparatus 200-i receives the input of the correction and generates the analysis result information DA1 in which a measured value of the regions of the corrected heart and lung and the cardio-thoracic ratio, and additional information indicating that the correction has been performed are housed.

In a case of extracting a region included in the medical image, the medical image identification engine determines the detection result of the range and contour of the region and property of the detection results. In a case where an error is found in the detection result of the range or contour of the region or the determination result of property thereof (for example, whether or not it is a tumor) as the result of image interpretation by a physician, the physician performs the correction in the diagnosis support apparatus 200-i. The controller 202 of the diagnosis support apparatus 200-i receives the input of the correction and generates the analysis result information DA1 in which the corrected analysis result and the additional information indicating that the correction has been performed are housed.

Here, the correction of the detection result of the range or the contour of the region included in the medical image will be described with reference to FIGS. 4 and 5.

Figure 4:
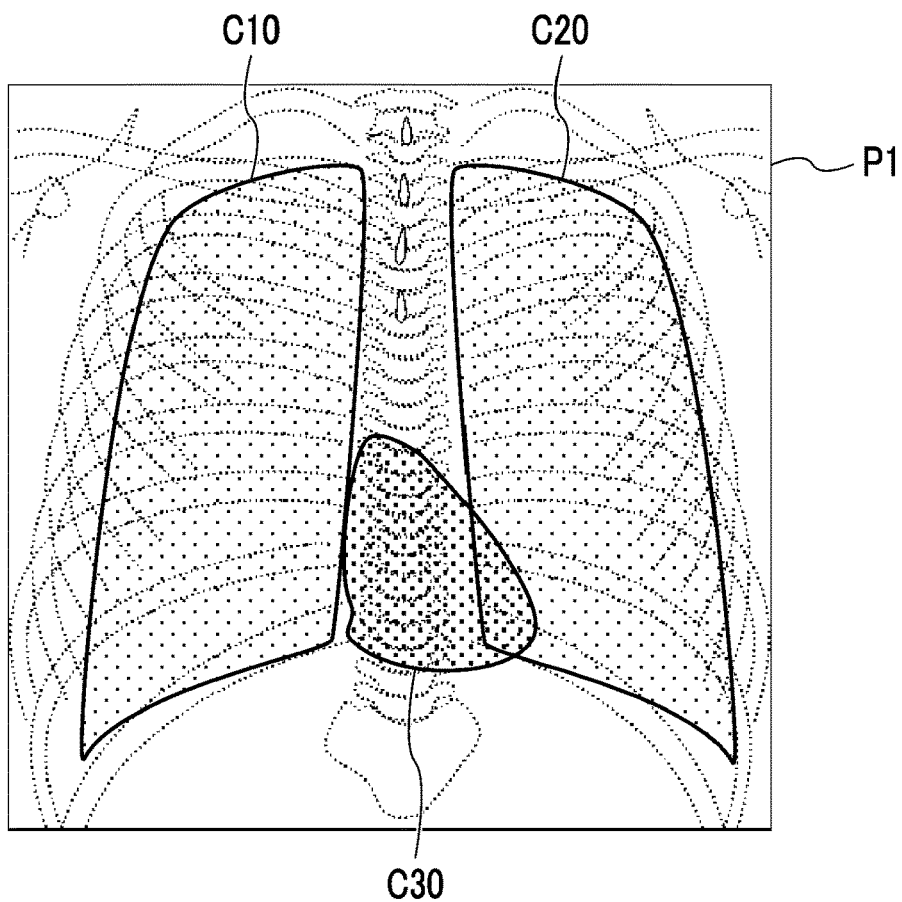
FIG. 4 is a diagram illustrating regions (lung and heart) extracted by a medical image identification engine.

FIG. 4 is a diagram illustrating regions (lung and heart) extracted by a medical image identification engine. The medical image identification engine analyzes a medical image P1, which is a chest X-ray image, and automatically detects regions indicating the right lung, the left lung, and the heart. The result of the automatic detection is displayed on the display unit 210 (refer to FIG. 10) of the diagnosis support apparatus 200-i. In the example illustrated in FIG. 4, contour lines C10, C20, and C30 corresponding respectively to the right lung, the left lung, and the heart are superimposed on the medical image P1. The physician can perform the correction using the operation unit 204 (see FIG. 10) while looking at the display unit 210 of the diagnosis support apparatus 200-i.

Figure 5:
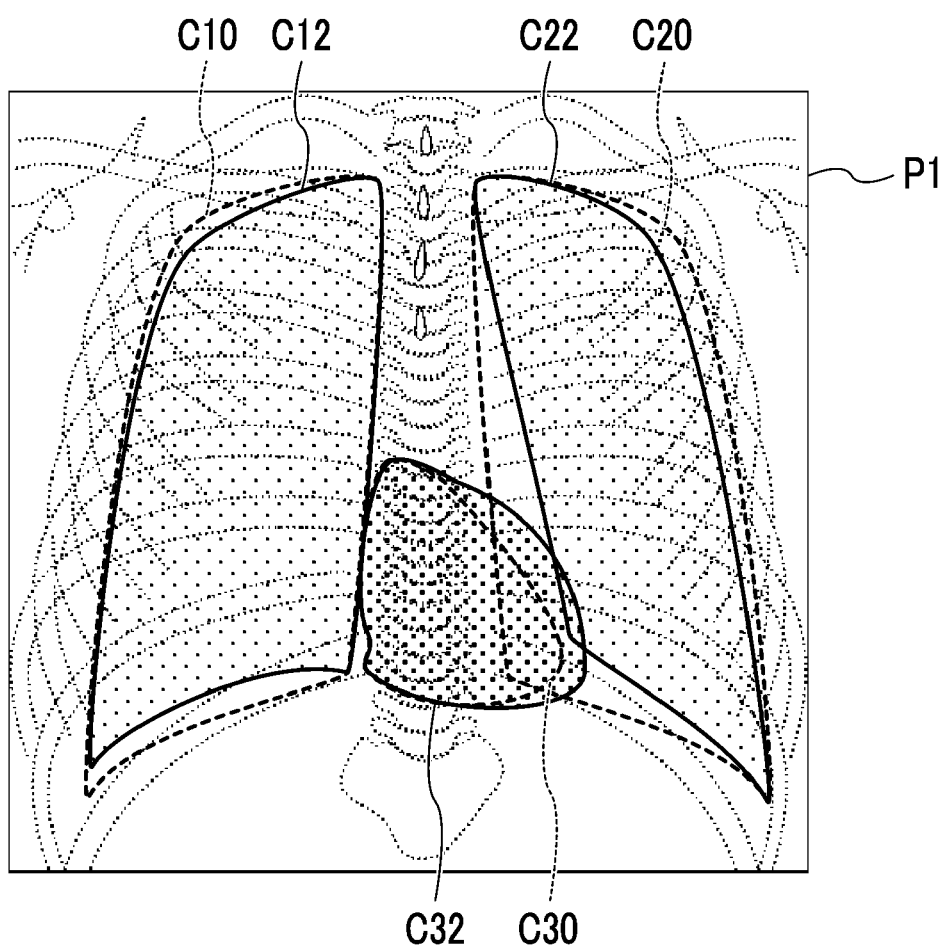
FIG. 5 is a diagram illustrating a state where the regions extracted by the medical image identification engine has been corrected.

FIG. 5 is a diagram illustrating a state where the regions extracted by the medical image identification engine has been corrected. C12, C22, and C32 illustrated in FIG. 5 are the contour lines corresponding respectively to the right lung, the left lung, and the heart after the correction. The contour lines C10, C20 and C30 before the correction are indicated by broken lines.

In a case where it is detected that the contour lines C12, C22, and C32 indicating the region included in the medical image have been corrected, the controller 202 of the diagnosis support apparatus 200-*i* generates the analysis result information DA1 in which an analysis result including position information of the contour lines C12, C22, and C32 after the correction and additional information indicating that the correction has been performed are housed.

Figure 6:
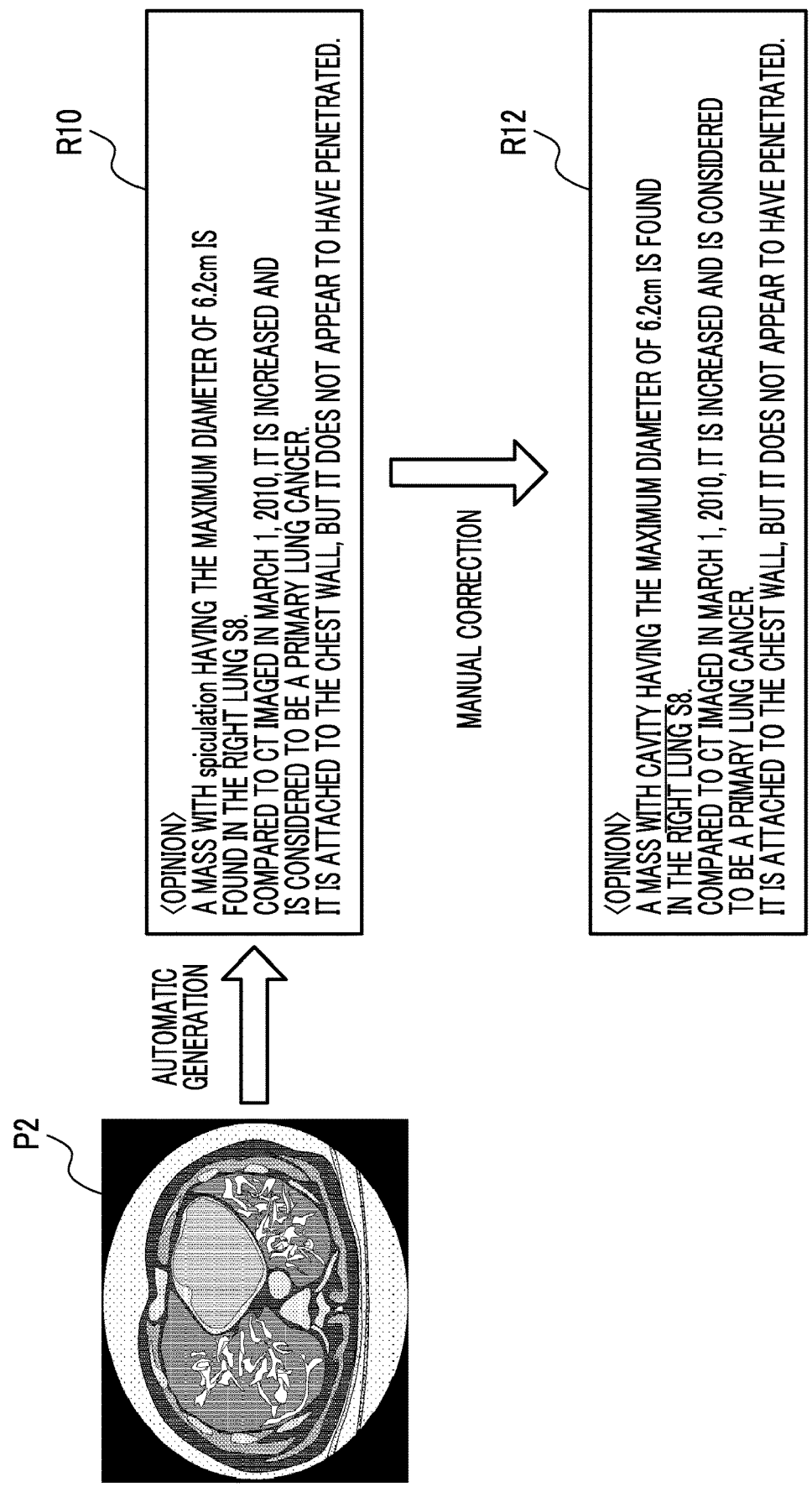
FIG. 6 is a diagram for explaining automatic generation and correction of a diagnosis report.

In addition, the medical image identification engine can automatically generate a diagnosis report (findings) by analyzing the medical image. FIG. 6 is a diagram for explaining automatic generation and correction of a diagnosis report.

In the example illustrated in FIG. 6, the medical image identification engine analyzes a medical image P2 which is a tomographic image (CT image) of the chest and automatically generates a diagnosis report (findings) R10. Here, the medical image identification engine can generate the diagnosis report by using a diagnosis report creating unit similar to an image diagnosis support apparatus described in JP-H07-323024A, for example. The diagnosis report may include, for example, information (sentence) indicating a determination result (for example, whether or not it is a tumor) of the position, size, and type of the region to be diagnosed in the medical image and/or property thereof. Further, the diagnosis report may include, for example, information for displaying the medical image and the region to be diagnosed in the medical image (for example, a mark indicating a coordinate or a position). The medical image identification engine may automatically generate one or more words (keywords) as the analysis result of the medical image P2. Here, the automatically generated keyword may be, for example, a term representing a medical image feature detected from the medical image (for example, cell lung (honeycomb lung)) or a disease name (for example, a mass or a spiculation), and may be a qualitative and sensory phrase such as "a wide range" or "local". The automatically generated diagnosis report R10 or keyword may include a numerical value including the size, length, area, or volume of a region including the features or diseases of these images.

The physician can display the diagnosis report R10 on the display unit 210 of the diagnosis support apparatus 200-*i*, and perform the correction using the operation unit 204. In the corrected diagnosis report R12 illustrated in FIG. 6, a part "with spiculation" among sentences included in the diagnosis report R10 is corrected to "with cavity".

In a case where it is detected that the diagnosis report R10 have been corrected, the controller 202 of the diagnosis support apparatus 200-*i* generates the analysis result information DA1 in which an analysis result including the diagnosis report R12 after the correction and additional information indicating that the correction has been performed are housed.

Here, an example has been described in which the physician corrects the sentence itself output as the automatically generated diagnosis report R10, but the automatically generated diagnosis report R10 and the method of correcting the same are not limited thereto. For example, an operation of automatically generating candidate words (keywords) for a physician to input in a diagnosis report by the image analysis and displaying the words on the display unit 210 of the diagnosis support apparatus 200-*i*, and inputting the acceptance or rejection of each word by the physician (for example, a check box is pre-selected for each candidate word, and then the check box is turned off for those that the physician decides not to employ) is also included in the correction of the automatically generated diagnosis report.

The medical image processing apparatus 100-*i* acquires the DICOM file F2 including the medical image IMG1, the patient information DP1, and the analysis result information DA1 from the diagnosis support apparatus 200-*i*. Then, the medical image processing apparatus 100-*i* creates the concealment data DCi by performing the concealment processing for concealing the identification information capable of identifying a patient on data in which the correction has been input by the physician in the diagnosis support apparatus 200-*i* among the medical image IMG1, the patient information DP1, and the analysis result information DA1.

As illustrated in FIG. 3, the concealment data DCi includes a concealed medical image IMG2, patient information DP2, and analysis result information DA2. Similarly to the DICOM files F1 and F2, the concealment data DCi can be created in a data format conforming to, for example, a digital imaging and communications in medicine (DICOM) or a medical image processing systems (MIPS) standard of Japan Medical Imaging and Radiological Systems Industries Association.

The concealment data DCi can be used, for example, as teacher data for supervised learning that inputs the image of an examination part of a patient extracted from the medical image and outputs analysis result information for the examination part of the patient that has been approved or corrected by the physician. The "output" in the teacher data may be called a teacher signal, a teaching signal, correct data, or a label.

The medical image processing apparatus 100-*i* transmits the concealment data DCi to the medical support server 300. The data collection unit 302 of the medical support server 300 collects concealment data DC1, DC2, . . . , DCn respectively transmitted from the medical image processing apparatus 100-1, 100-2, . . . , 100-*n* of the medical institutions M1, M2, . . . , Mn.

The learning unit 304 of the medical support server 300 causes the pre-learning analysis unit 350 to perform learning using the concealment data DC1, DC2, . . . , DCn collected from the medical institutions M1, M2, . . . , Mn.

In the learning unit 304, for example, a medical image of the examination part of the patient read out from the concealment data DC1, DC2, . . . , DCn which is the teacher data, and feature quantity in the medical image are input to the analysis unit 350. Then, the learning unit 304 performs learning on the input medical image of the examination part so as to obtain the same output as information indicating the diagnosis result corresponding to the examination part. Here, as the feature quantity in the medical image, for example, the average of brightness or luminance in the medical image, the area of the examination part or lesion, the perimeter and the flatness, and the length of the long axis in a case where the examination part or lesion is approximated to an ellipse, and the inclination of the long axis with respect to the examination part of the patient or a feature part of the lesion (for example, contours of spine, bones or internal organs included in the examination part of the patient, center of gravity or central axis) can be used.

The pre-learning analysis unit 350 and the learned analysis unit 352 are data used for generating the diagnosis support information in the diagnosis support apparatus 200-*i*, and includes, for example, information indicating the structure of the diagnosis support apparatus 200-1, 200-2, . . . , 200-*n* (a diagnosis support information generation unit 214) and a value of a variable. As the pre-learning analysis unit 350 and the learned analysis unit 352, for example, those using a neural network, deep learning, a decision tree, a linear classifier, a support vector machine (SVM), a discriminant analysis, and the like can be used.

The diagnosis support apparatus 200-i acquires the learned analysis unit 352 from the medical support server 300, and updates the medical image identification engine.

In a case where another medical image (a medical image that has not been used for learning, for example, a medical image of a patient to be newly examined) is acquired by the examination apparatus 150, the diagnosis support apparatus 200-i analyzes another medical image using the learned analysis unit 352. Then, the diagnosis support apparatus 200-i generates diagnosis support information indicating an analysis result of another medical image, and presents it to the physician of the medical institution Mi.

The medical image processing apparatus 100-1, 100-2, . . . , 100-n, the diagnosis support apparatus 200-1, 200-2, . . . , 200-n, and the medical support server 300 can be communicated via a network, but the present invention is not limited to thereto. For example, an administrator of the medical support server 300 may visit each of the medical institutions M1, M2, . . . , Mn to collect the concealment data DC1, DC2, . . . , DCn and provide the learned analysis unit 352 (the update of the medical image identification engine) to the diagnosis support apparatus 200-1, 200-2, . . . , 200-n.

In the present embodiment, the medical image processing apparatus 100-i and the diagnosis support apparatus 200-i are separate apparatuses, but they may be the same apparatus.

Further, the medical image processing apparatus 100-i and the diagnosis support apparatus 200-i according to the present embodiment may be included in a picture archiving and communication systems (PACS) in the medical institution Mi.

(Medical Image Processing Apparatus)

Figure 7:
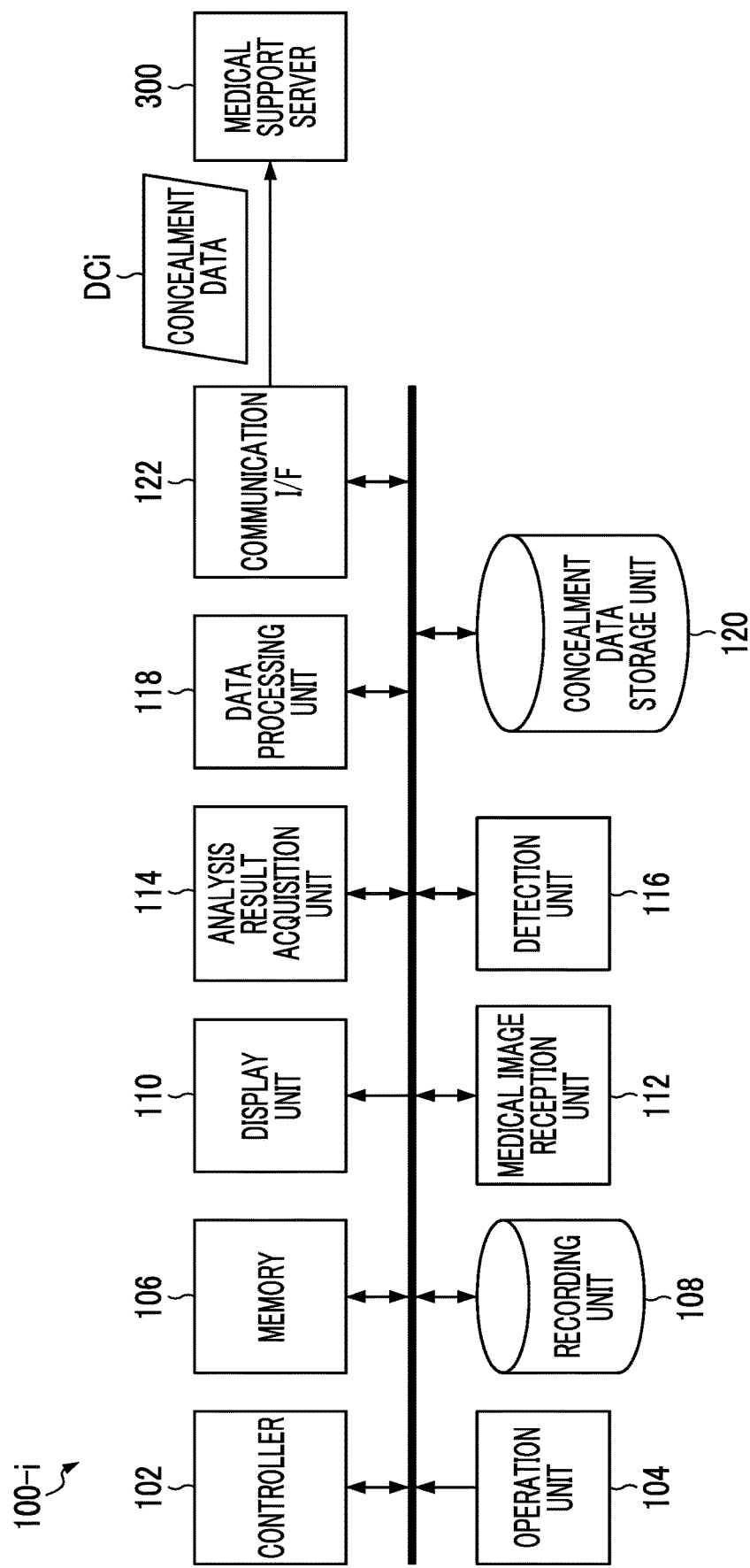
FIG. 7 is a block diagram illustrating a medical image processing apparatus according to the first embodiment of the present invention.

Next, the medical image processing apparatus will be described with reference to FIG. 7. FIG. 7 is a block diagram illustrating a medical image processing apparatus according to the first embodiment of the present invention.

The medical image processing apparatus 100-i according to the present embodiment includes a controller 102, an operation unit 104, a memory 106, a recording unit 108, a display unit 110, a medical image reception unit 112, an analysis result acquisition unit 114, a detection unit 116, a data processing unit 118, a concealment data storage unit 120, and a communication interface (communication I/F: interface) 122.

The controller 102 includes a central processing unit (CPU) that controls the operation of each unit of the medical image processing apparatus 100-i. The controller 102 is capable of transmitting and receiving control signals and data to and from each unit of the medical image processing apparatus 100-i via a bus. The controller 102 receives an operation input from an operator (physician or the like) via the operation unit 104, and controls the operation of each unit by transmitting a control signal corresponding to the operation input to each unit of the medical image processing apparatus 100-i via the bus.

The operation unit 104 is an input apparatus that receives the operation input from the operator, and includes a keyboard for inputting characters and the like, and a pointing device (for example, a mouse, a trackball, or the like) for operating a pointer, an icon, or the like displayed on the display unit 110. As the operation unit 104, a touch panel may be provided on the surface of the display unit 110 instead of the keyboard and the pointing device, or in addition to the keyboard and the pointing device.

The memory 106 includes a random access memory (RAM) used as a work area for various calculations performed by the controller 102 and the like, and a video random access memory (VRAM) used as a region for temporarily storing the image data output to the display unit 110.

The recording unit 108 is a storage device that houses a control program used by the controller 102, data (DICOM file F2) received from the diagnosis support apparatus 200-i, and the like. As the recording unit 108, for example, an apparatus including a magnetic disk such as a hard disk drive (HDD), an apparatus including a flash memory such as an embedded multi media card (eMMC), a solid state drive (SSD), or the like can be used.

The display unit 110 is an apparatus for displaying an image. As the display unit 110, for example, a liquid crystal monitor can be used.

The communication I/F 122 is a unit for communicating with another apparatus via a network, and performs conversion processing of data to be transmitted and received according to a communication method. As a method of transmitting and receiving data between the medical image processing apparatus 100-i and another apparatus, wired communication or wireless communication (for example, local area network (LAN), wide area network (WAN), internet connection, and or the like) can be used.

The medical image reception unit 112 receives the input of the medical image IMG1 and the patient information DP1 from the DICOM file F2 transmitted from the diagnosis support apparatus 200-i. The medical image IMG1 and the like input to the medical image reception unit 112 are images that have been interpreted by a physician in the diagnosis support apparatus 200-i.

The analysis result acquisition unit 114 acquires the analysis result information DA1 from the DICOM file F2 transmitted from the diagnosis support apparatus 200-i.

The detection unit 116 determines whether or not the analysis result information DA1 includes additional information indicating that the diagnosis support information DA0 has been corrected in the diagnosis support apparatus 200-i.

In the present embodiment, additional information indicating the presence or absence of approval or correction is added to the analysis result information DA1, but the present invention is not limited to thereto. For example, without using the additional information, the detection unit 116 may acquire both the diagnosis support information DA0 and the analysis result information DA1 and compare these to determine whether or not the correction is performed.

The data processing unit 118 performs the concealment processing for concealing the patient identification information on the DICOM file F2 in which the additional information indicating that the diagnosis support information DA0 has been corrected has been detected. Then, the data processing unit 118 generates the concealment data DCi including the concealed medical image IMG2, patient information DP2, and analysis result information DA2.

The concealment data storage unit 120 is a storage device that stores the concealment data DCi that has been subjected to the concealment processing of the patient identification information by the data processing unit 118. The concealment data storage unit 120 may be, for example, a storage region provided in the recording unit 108.

In the present embodiment, the concealment data DCi is transmitted to the medical support server 300 after being stored in the concealment data storage unit 120 of the medical image processing apparatus 100-i, but the present invention is not limited to thereto. The concealment data storage unit 120 may be, for example, provided on a cloud where the concealment data DCi can be uploaded from the medical image processing apparatus 100-i and the data collection unit 302 of the medical support server 300 can download the concealment data DCi. In this case, for example, a cloud-type VPN can be used.

(Concealment Processing)

Next, the concealment processing by the data processing unit 118 will be described. First, the concealment processing for the patient information DP1 will be described.

In the present embodiment, the patient information DP1 is housed as tag information in the DICOM file F2. The data processing unit 118 deletes identification information that can identify a patient from the tag information of the DICOM file F2.

Tables 1 to 3 show examples of the tags of the DICOM file. Table 1 shows an example of a tag related to patient identification information, Table 2 shows an example of a tag related to a medical institution Mi, and Table 3 shows an example of a tag related to the content of an examination.

The data processing unit 118 deletes the tags related to the patient identification information shown in Table 1 other than those including information necessary for analyzing the medical image IMG1. For example, among the tags in Table 1, tags such as age of the patient, smoking status, additional medical history of the patient, and pregnancy status may be left. All tags related to the patient identification information shown in Table 1 may be deleted.

TABLE 1

Example of Tag Related to Patient Identification Information

| Tag | Title |
|---|---|
| (0010, 0020) | Patient ID |
| (0010, 0010) | Patient's Name |
| (0010, 0030) | Patient's Birth Date |
| (0010, 0032) | Patient's Birth Time |
| (0010, 0040) | Patient's Sex |
| (0010, 1010) | Patient's Age |
| (0010, 1020) | Patient's Size |
| (0010, 1030) | Patient's Weight |
| (0010, 1040) | Patient's Address |
| (0010, 2154) | Patient's Telephone Numbers |
| (0010, 2180) | Occupation |
| (0010, 2160) | Ethnic Group |
| (0010, 2000) | Medical Alerts |
| (0010, 2110) | Allergies |
| (0010, 21A0) | Smoking Status |
| (0010, 21B0) | Additional Patient History |
| (0010, 21C0) | Pregnancy Status |
| (0010, 4000) | Patient Comments |

TABLE 2

Example of Tag Related to Medical Institution

| Tag | Title |
|---|---|
| (0008, 0080) | Institution Name |
| (0008, 0081) | Institution Address |

Further, the data processing unit 118 may consider that the patient identification information is included in tags such as a reception number, an examination description, and a diagnosis description at the time of consultation among tags related to the content of the examination. Therefore, the data processing unit 118 acquires the patient identification information (for example, patient ID, patient name, birthday, address, telephone number, occupation, and the like), and compares it with tag information such as the examination description and the diagnosis description at the time of consultation. Thereafter, in a case where the patient identification information is included, the data processing unit 118 deletes the entire tag information or replaces the patient information included in the tag information with a hidden character. The data processing unit 118 may manually delete the information after a physician or an operator of the medical institution Mi checks the content of the tag.

TABLE 3

Example of Tag Related to Content of Examination

| Tag | Title |
|---|---|
| (0008, 040) | Institutional Department Name |
| (0008, 0050) | Accession Number |
| (0008, 0020) | Study Date |
| (0008, 0030) | Study Time |
| (0008, 0060) | Modality |
| (0008, 0070) | Manufacturer |
| (0018, 0015) | Body Part Examined |
| (0010, 9431) | Examined Body Thickness |
| (0008, 1030) | Study Description |
| (0008, 1080) | Admitting Diagnoses Description |
| (0008, 1048) | Physician(s) of Record |
| (0008, 1050) | Performing Physician's Name |
| (0008, 1060) | Name of Physician(s) Reading Study |
| (0008, 1070) | Operator's Name |

In addition, it is conceivable that a private tag also includes the patient identification information. Therefore, the data processing unit 118 acquires the patient identification information (for example, patient ID, patient name, address, telephone number, and the like), and compares it with the content of the private tag. Thereafter, in a case where the patient identification information is included, the data processing unit 118 deletes the entire tag information or replaces the patient information included in the tag information with a hidden character. The data processing unit 118 may delete all the private tags, or may manually delete the information after the physician or the operator of the medical institution Mi checks the content of the private tag.

Figure 8:
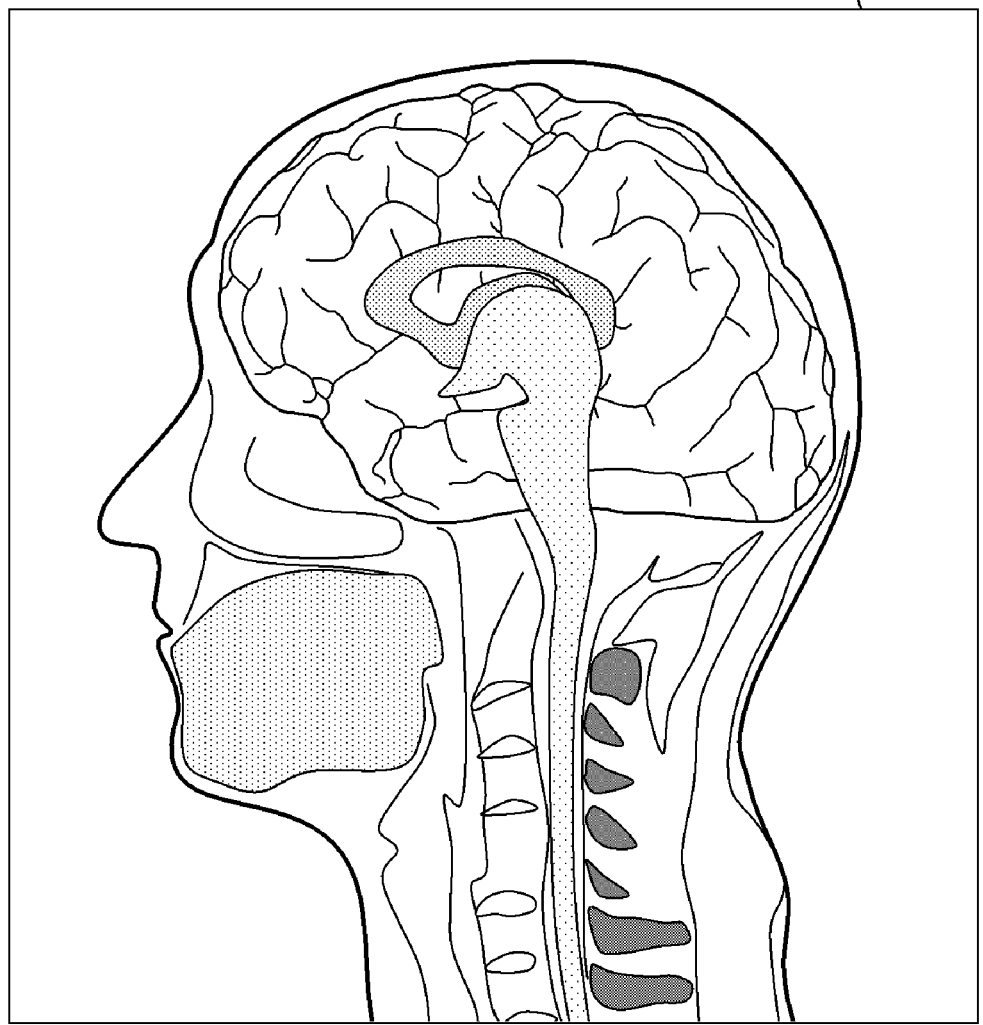
FIG. 8 is a diagram illustrating an example of medical images.

Next, the concealment processing of the patient identification information from the medical image will be described with reference to FIGS. 8 and 9. FIG. 8 illustrates an example of a medical image, and FIG. 9 illustrates an example of a concealed medical image.

The medical image IMG1 illustrates in FIG. 8 is a tomographic image of the patient's head and includes a part of a body surface. In a case where the part of the body surface is extracted from a plurality of tomographic images and combined, a patient's face is reproduced.

Figure 9:
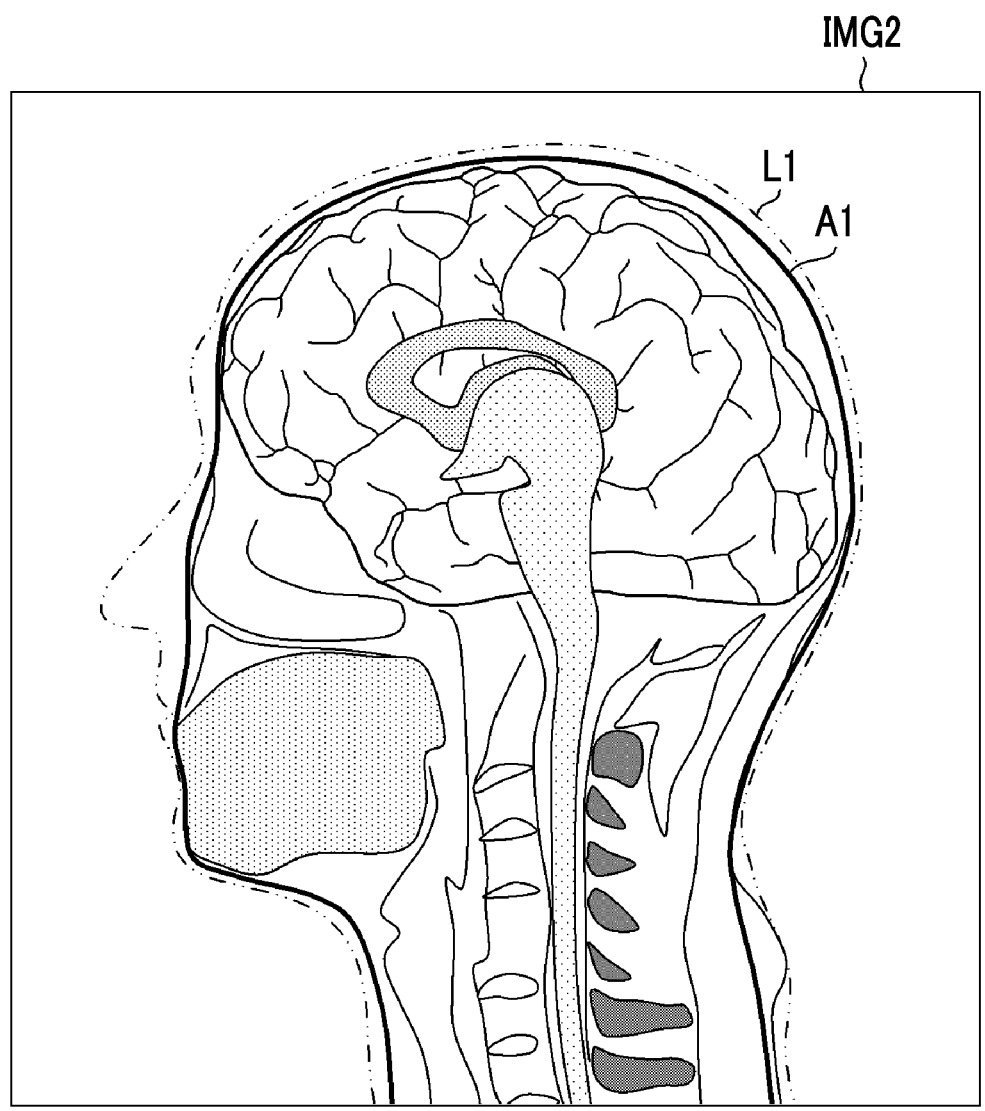
FIG. 9 is a diagram illustrating an example of a concealed medical image.

Therefore, as illustrated in FIG. 9, the data processing unit 118 processes the medical image IMG1 and deletes a region A1 near a body surface L1 to create a concealed medical image IMG2 in which body surface data is concealed. Here, the region A1 near the body surface L1 can be, for example, a region from the body surface L1 to a contour of a tissue to be diagnosed (for example, brain, trachea, bone, or the like). The data processing unit 118 performs a process of filling the region A1 with the same color as the background color or overlapping another image. This makes it possible to conceal the image of the body surface of the patient.

In the concealment data DCi, the patient identification information is encrypted and housed, and in a case where it is necessary for diagnosis and learning, an operator who has access authority to the patient identification information may be able to retrieve the patient information DP1. In addition, an electronic signature may be added to the concealment data DCi in order to enable tampering detection.

(Diagnosis Support Apparatus)

Figure 10:
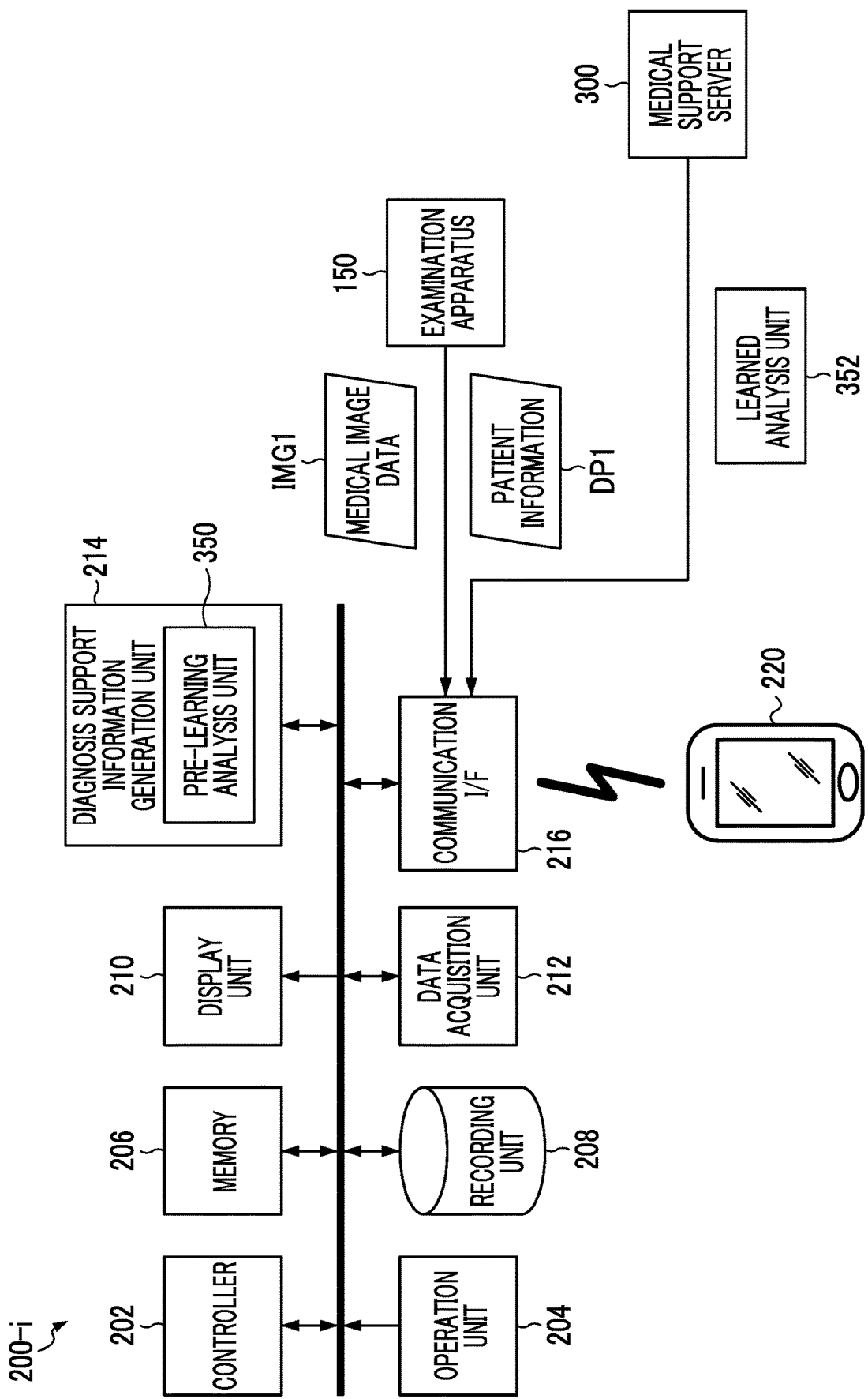
FIG. 10 is a block diagram illustrating a diagnosis support apparatus according to the first embodiment of the present invention.

Next, the diagnosis support apparatus will be described with reference to FIG. 10. FIG. 10 is a block diagram illustrating a diagnosis support apparatus according to the first embodiment of the present invention.

The diagnosis support apparatus 200-$i$ according to the present embodiment includes the controller 202, the operation unit 204, a memory 206, a recording unit 208, the display unit 210, a data acquisition unit 212, a diagnosis support information generation unit 214, and a communication interface (communication I/F: interface) 216.

The controller 202 includes a central processing unit (CPU) that controls the operation of each unit of the diagnosis support apparatus 200-$i$. The controller 202 is capable of transmitting and receiving control signals and data to and from each unit of the diagnosis support apparatus 200-$i$ via a bus. The controller 202 receives an operation input from an operator via the operation unit 104, and controls the operation of each unit by transmitting a control signal corresponding to the operation input to each unit of the diagnosis support apparatus 200-$i$ via the bus.

The operation unit 204 is an input apparatus that receives the operation input from the operator, and includes a keyboard for inputting characters and the like, and a pointing device (for example, a mouse, a trackball, or the like) for operating a pointer, an icon, or the like displayed on the display unit 210. As the operation unit 204, a touch panel may be provided on the surface of the display unit 210 instead of the keyboard and the pointing device, or in addition to the keyboard and the pointing device.

The memory 206 includes a random access memory (RAM) used as a work area for various calculations performed by the controller 202 and the like, and a video random access memory (VRAM) used as a region for temporarily storing the image data output to the display unit 210.

The recording unit 208 is a storage device that houses a control program used by the controller 202, data (DICOM file F1) received from the examination apparatus 150, and the like. As the recording unit 208, for example, an apparatus including a magnetic disk such as a hard disk drive (HDD), an apparatus including a flash memory such as an embedded multi media card (eMMC), a solid state drive (SSD), or the like can be used.

The display unit 210 is an apparatus for displaying an image. As the display unit 210, for example, a liquid crystal monitor can be used.

The communication I/F 216 is a unit for communicating with another apparatus via a network, and performs conversion processing of data to be transmitted and received according to a communication method. As a method of transmitting and receiving data between the medical image processing apparatus 100-$i$ and another apparatus, wired communication or wireless communication (for example, local area network (LAN), wide area network (WAN), internet connection, and or the like) can be used.

The physician terminal 220 is a terminal for a physician of the medical institution Mi to display data such as medical images and to perform an operation input. The physician terminal 220 acquires and displays the data such as medical images from the diagnosis support apparatus 200-$i$ via the communication I/F 216, and receives the operation input from the physician. Thereby, the physician terminal 220 can perform processing and an update of the data of the diagnosis support apparatus 200-$i$.

The data acquisition unit 212 acquires the DICOM file F1 including the medical image IMG1 of the patient and the patient information DP1 from the examination apparatus 150.

The diagnosis support information generation unit 214 analyzes the medical image IMG1 using the medical image identification engine (the pre-learning analysis unit 350 or the learned analysis unit 352), generates diagnosis support information DA0 including the analysis result, and causes the display unit 210 to display it with the medical image IMG1 and the patient information DP1. Thereby, the physician can interpret the medical image IMG1 while referring to the diagnosis support information DA0.

(Medical Image Processing Method)

Figure 11:
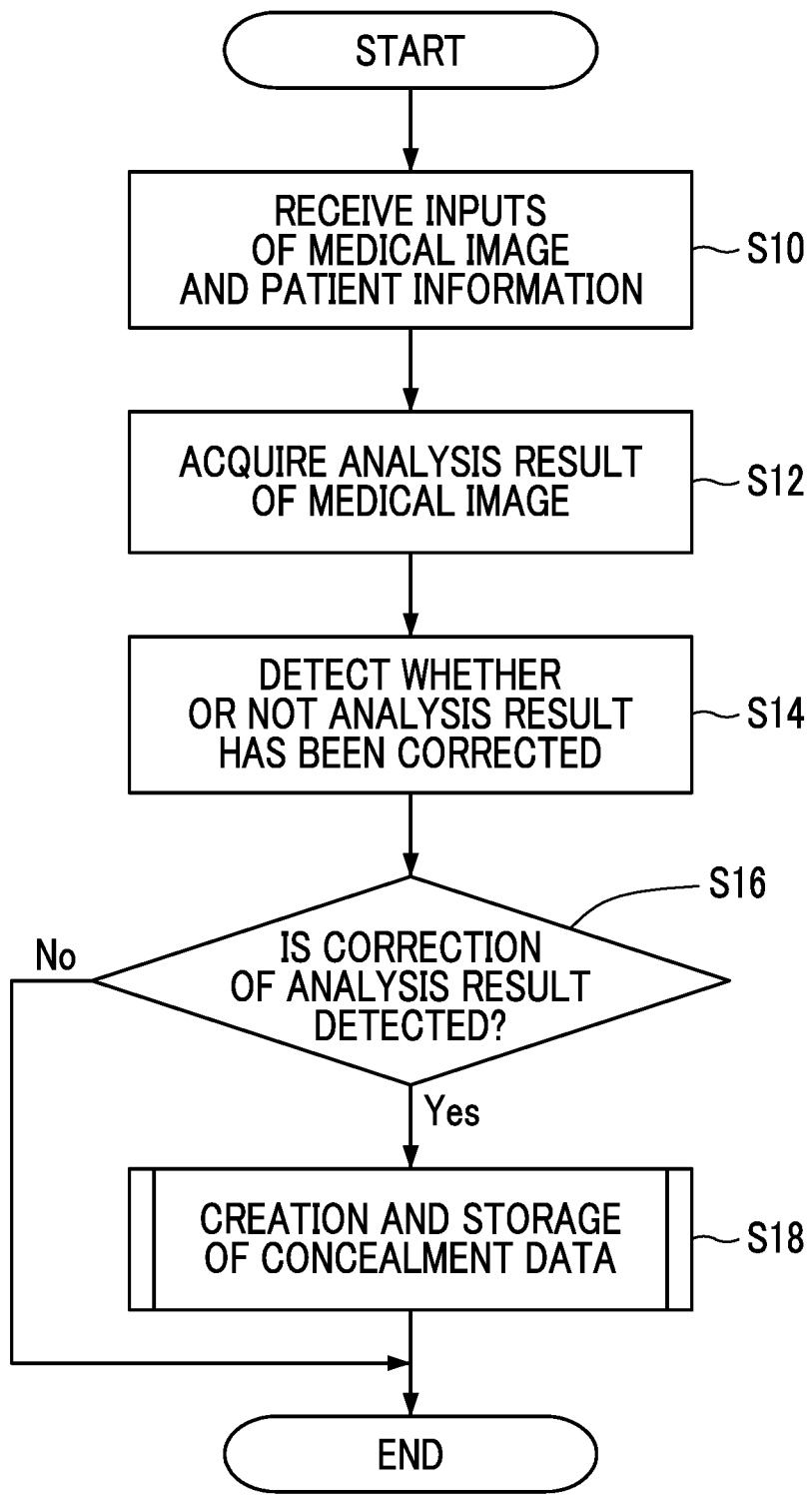
FIG. 11 is a flowchart illustrating a flow of processing in a medical image processing method according to the first embodiment of the present invention.

Next, the medical image processing method according to the present embodiment will be described with reference to FIG. 11. FIG. 11 is a flowchart illustrating a flow of processing in a medical image processing method according to the first embodiment of the present invention.

First, the medical image processing apparatus 100-$i$ acquires the DICOM file F2 including the medical image IMG1 interpreted by the physician and the analysis result information DA1 in which the diagnosis support information DA0 has been approved or corrected by the physician from a diagnosis support apparatus 200-$i$. The medical image reception unit 112 receives inputs of the medical image IMG1 and the patient information DP1 (step S10: reception step). The analysis result acquisition unit 114 acquires the analysis result information DA1 of the medical image IMG1 (step S12: analysis result information step).

Next, the detection unit 116 determines, in the diagnosis support apparatus 200-$i$, whether or not additional information indicating that the analysis result (diagnosis support information DA0) has been corrected by the medical image identification engine is included in the analysis result information DA1 (step S14: detection step). Then, in a case where the correction of the analysis result is not detected (No in step S16), the processing ends.

On the other hand, in a case where the correction of the analysis result is detected (Yes in step S16), the data processing unit 118 performs concealment processing on the DICOM file F2 to create the concealment data DCi, and stores the concealment data DCi in the concealment data storage unit 120 (step S18: data processing step).

(Diagnosis Support Method)

Figure 12:
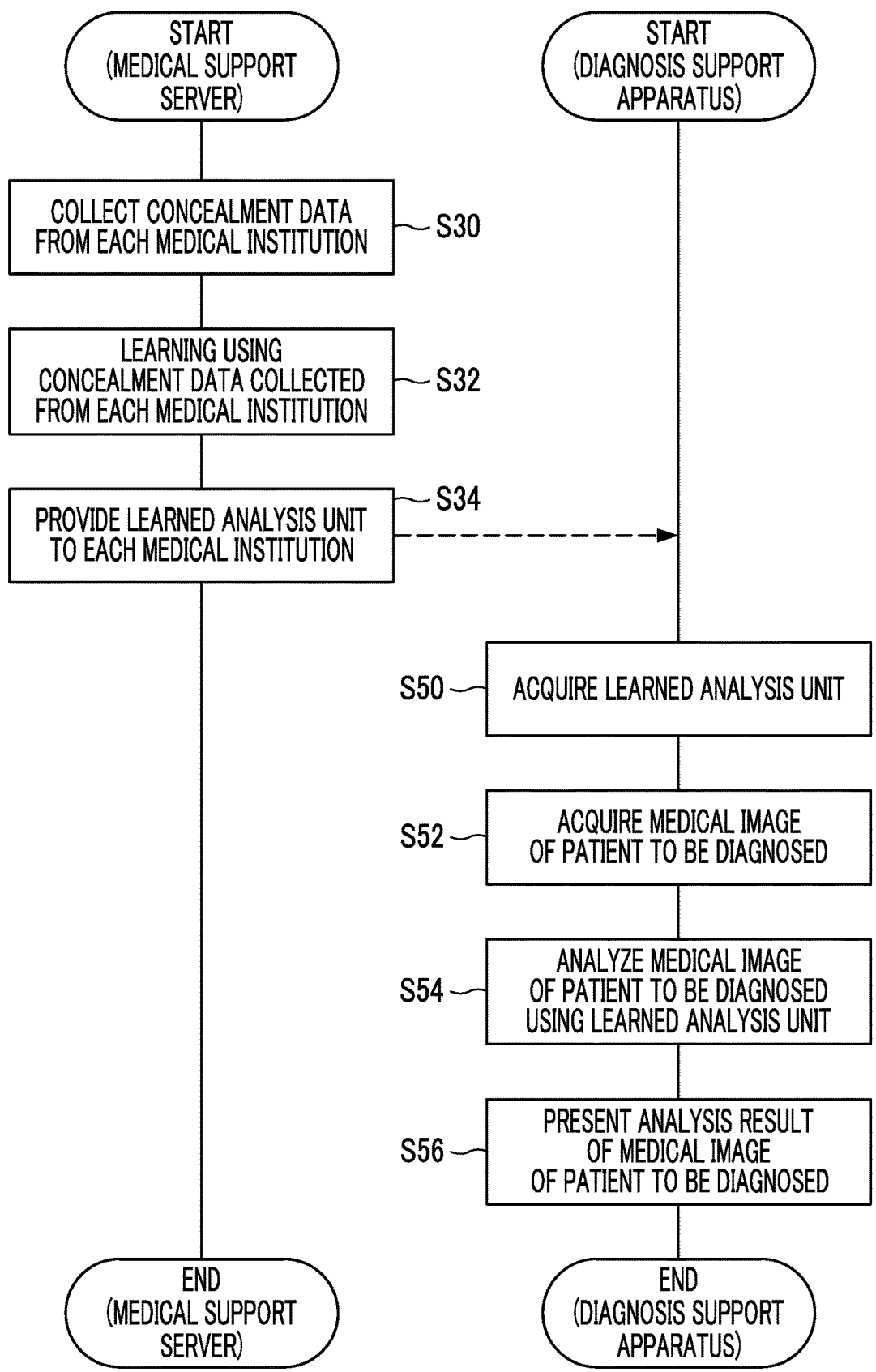
FIG. 12 is a flowchart illustrating a flow of processing in a diagnosis support method according to the first embodiment of the present invention.

Next, the diagnosis support method according to the present embodiment will be described with reference to FIG. 12. FIG. 12 is a flowchart illustrating a flow of processing in a diagnosis support method according to the first embodiment of the present invention.

First, in the medical support server 300, the data collection unit 302 collects concealment data DC1, DC2, . . . , DCn respectively from the medical institutions M1, M2, . . . , Mn (step S30).

Next, the learning unit 304 causes the medical image identification engine (the pre-learning analysis unit 350) to perform learning using the concealment data DC1, DC2, . . . , DCn collected respectively from the medical institutions M1, M2, . . . , Mn (step S32). Then, the learned analysis unit 352 is provided from the medical support server 300 to the medical institutions M1, M2, . . . , Mn (step S34).

Next, the diagnosis support apparatus 200-$i$ updates the medical image identification engine by acquiring the learned analysis unit 352 from the medical support server 300 via the communication I/F 216 and replacing it with the pre-learning analysis unit 350 of the diagnosis support information generation unit 214 (step S50).

Next, in a case where the data acquisition unit 212 of a diagnosis support apparatus 200A-i acquires a medical image of a patient to be diagnosed from the examination apparatus 150 (step S52), the diagnosis support information generation unit 214 analyzes the medical image of the patient to be diagnosed using the learned analysis unit 352 (step S54). Then, the diagnosis support information generation unit 214 causes the display unit 210 to display the analysis result of the medical image of the patient to be diagnosed as the diagnosis support information DA0 (step S56).

According to the present embodiment, the data corrected by a physician among the analysis results by the medical image identification engine of the medical institution Mi, that is, the data in which the analysis result by the medical image identification engine includes an error can be collected from the medical institution Mi and can be learned by the medical image identification engine.

Second Embodiment

Next, a second embodiment of the present invention will be described with reference to FIG. 13. In the second embodiment, a level at which the patient identification information is concealed can be changed in the data processing step of the first embodiment. In the following description, the same or similar configuration as those of the first embodiment are denoted by the same reference numeral, and description thereof is omitted.

Figure 13:
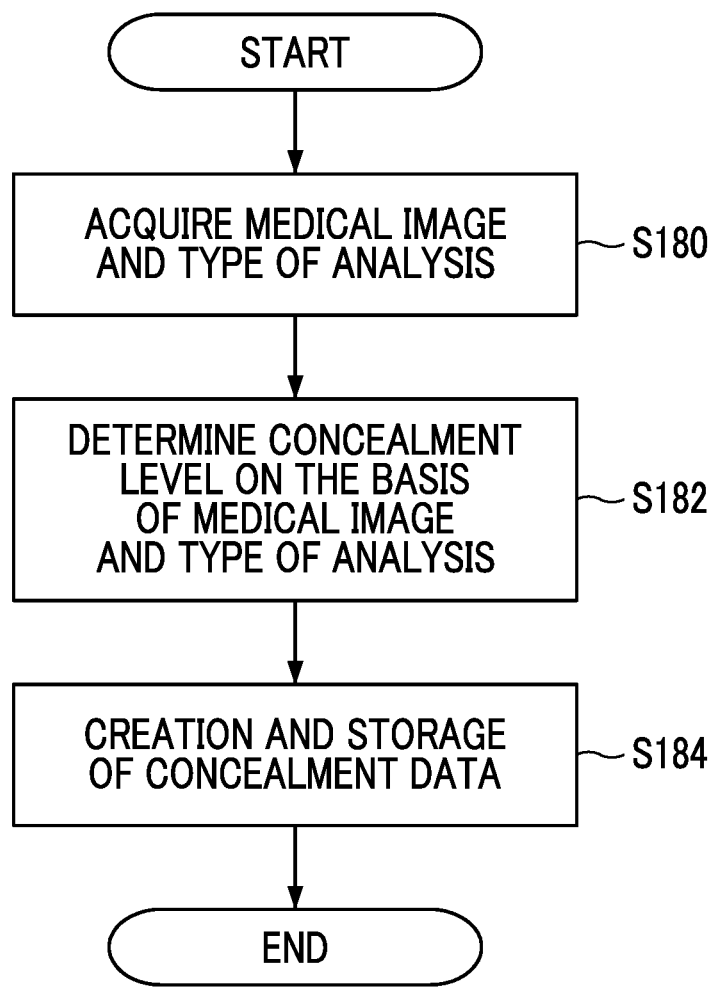
FIG. 13 is a flowchart illustrating a flow of processing (a data processing step) of creating and housing concealment data in a medical image processing method according to a second embodiment of the present invention.

FIG. 13 is a flowchart illustrating a flow of processing (a data processing step) of creating and housing concealment data in a medical image processing method according to a second embodiment of the present invention.

First, the data processing unit 118 acquires the medical image IMG1 included in the DICOM file F2, and acquires information on a type of the medical image IMG1 and information on a type of analysis (step S180). Here, the type of the medical image IMG1 includes, for example, information indicating an examination part (for example, a head, a chest, or the like) included in the medical image IMG1, information on a method of imaging the medical image IMG1, and information on a modality imaging the medical image IMG1 (for example, CT, MiII, or the like). The information on the type of analysis includes, for example, information on a lesion to be detected, information on a medical image identification engine used for detecting the lesion to be detected, and the like.

Next, the data processing unit 118 determines a concealment level on the basis of the medical image and the type of analysis (step S182). Then, the data processing unit 118 creates the concealment data DC and stores it in the concealment data storage unit 120 (step S184).

Table 4 shows an example of the concealment level, and Table 5 shows a correspondence relationship between the medical image identification engine and the concealment level.

In the example shown in Table 4, a type of patient identification information to be a target of the concealment processing increase in order from level I to level IV.

The data processing unit 118 determines the concealment level for each type of the medical image identification engine according to the concealment level shown in Table 5, and performs the concealment processing on the DICOM file F2. For example, in a case of detecting a brain disease, an image of the head is used. For this reason, level IV is applied, and body surface data is subject to concealment. Since the image of the head is not used in the detection of a fracture other than the head, the level II is applied.

TABLE 4

| Concealment Level | |
|---|---|
| Level I | Patient Name (Subject Name) |
| Level II | Patient Name (Subject Name), Age, Sex |
| Level III | Patient Name (Subject Name), Age, Sex, Disease |
| Level IV | Patient Name (Subject Name), Age, Sex, Disease, Body Surface Data |

TABLE 5

| Concealment Level for Each Type of Medical Image Identification Engine | |
|---|---|
| Detection of Cerebral Infarction, Stroke | Level IV |
| Measurement of Tumor | Level II |
| Detection of Fracture | Level II |
| Measurement of Cardio-Thoracic Ratio | Level I |

According to the present embodiment, it is possible to perform appropriate concealment processing on the patient identification information by selecting a target of the concealment processing according to the type of the medical image and the type of analysis.

Third Embodiment

Next, a third embodiment of the present invention will be described with reference to FIG. 14. In the third embodiment, in a case where the analysis result of the medical image identification engine is corrected, the concealment data is also created for images of the same patient at other time points, which can be used for learning.

Figure 14:
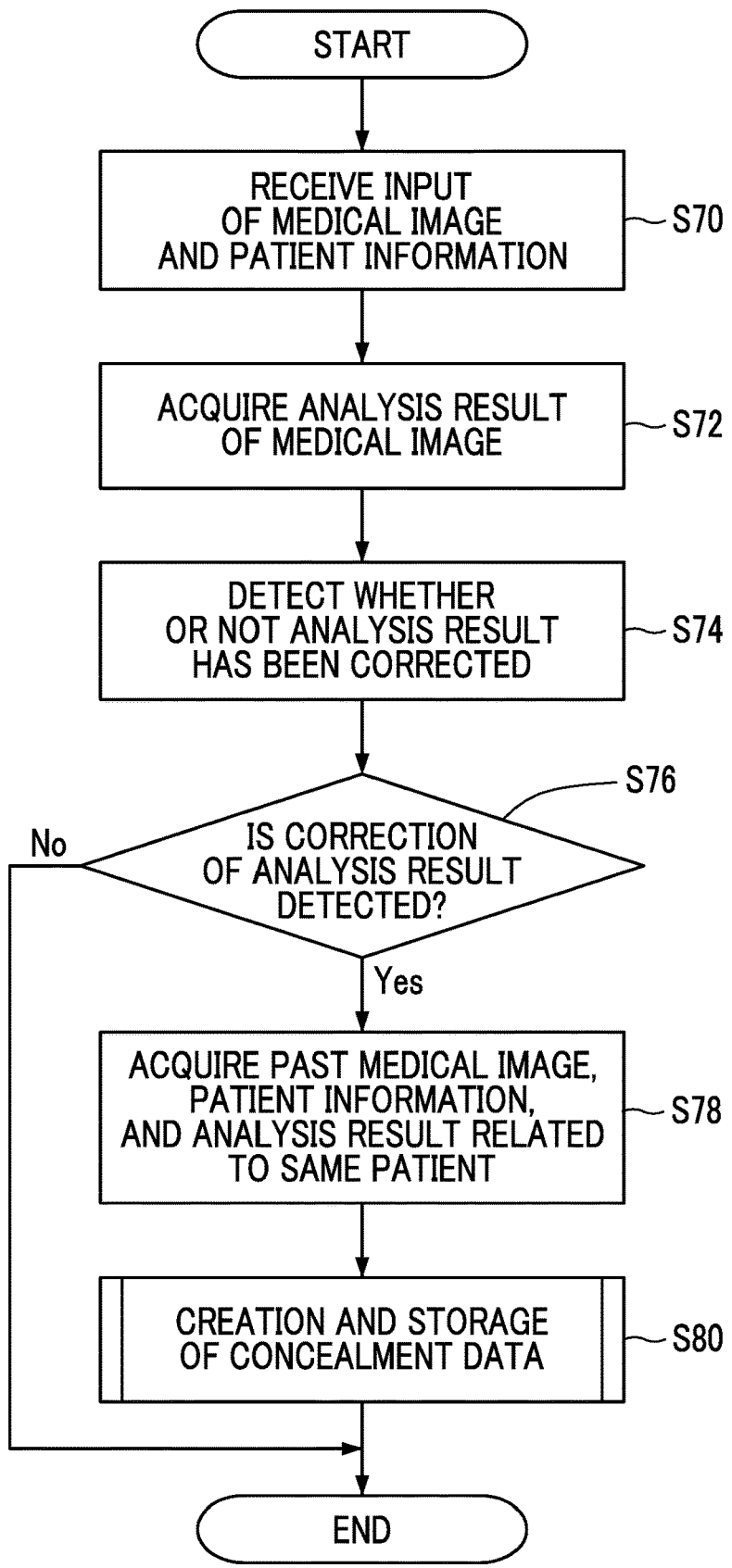
FIG. 14 is a flowchart illustrating a flow of processing in a medical image processing method according to a third embodiment of the present invention.

FIG. 14 is a flowchart illustrating a flow of processing in a medical image processing method according to the third embodiment of the present invention.

First, the medical image processing apparatus 100-i acquires the DICOM file F2 including the medical image IMG1 interpreted by the physician and the analysis result information DA1 in which the diagnosis support information DA0 has been approved or corrected by the physician from a diagnosis support apparatus. 200-i. The medical image reception unit 112 receives inputs of the medical image IMG1 and the patient information DP1 (step S70). The analysis result acquisition unit 114 acquires the analysis result information DA1 of the medical image IMG1 (step S72).

Next, the detection unit 116 determines, in the diagnosis support apparatus 200-i, whether or not additional information indicating that the analysis result (diagnosis support information DA0) has been corrected by the medical image identification engine is included in the analysis result information DA1 (step S74). Then, in a case where the correction of the analysis result is not detected (No in step S76), the processing ends.

On the other hand, in a case where the correction of the analysis result is detected (Yes in step S76), the data processing unit 118 reads out the patient identification information from the DICOM file F2 acquired in step S70. Then, the data processing unit 118 acquires the past DICOM file F2 for the same patient from the recording unit 108 on the basis of the patient identification information (step S78). In step S78, for example, the same examination part of the same patient, which is analyzed by the same medical image identification engine, may be acquired.

Next, the data processing unit 118 performs the concealment processing on the past DICOM file F2 acquired in step S78 in addition to the DICOM file F2 acquired in step S70 to create the concealment data DCi, and stores the concealment data DCi in the concealment data storage unit 120 (step S80).

In the example illustrated in FIG. 14, in a case where the correction of the analysis result is detected in the DICOM file F2 including the latest medical image IMG1, the concealment processing is also performed on the past DICOM file F2, but the present embodiment is not limited to thereto.

Figure 15:
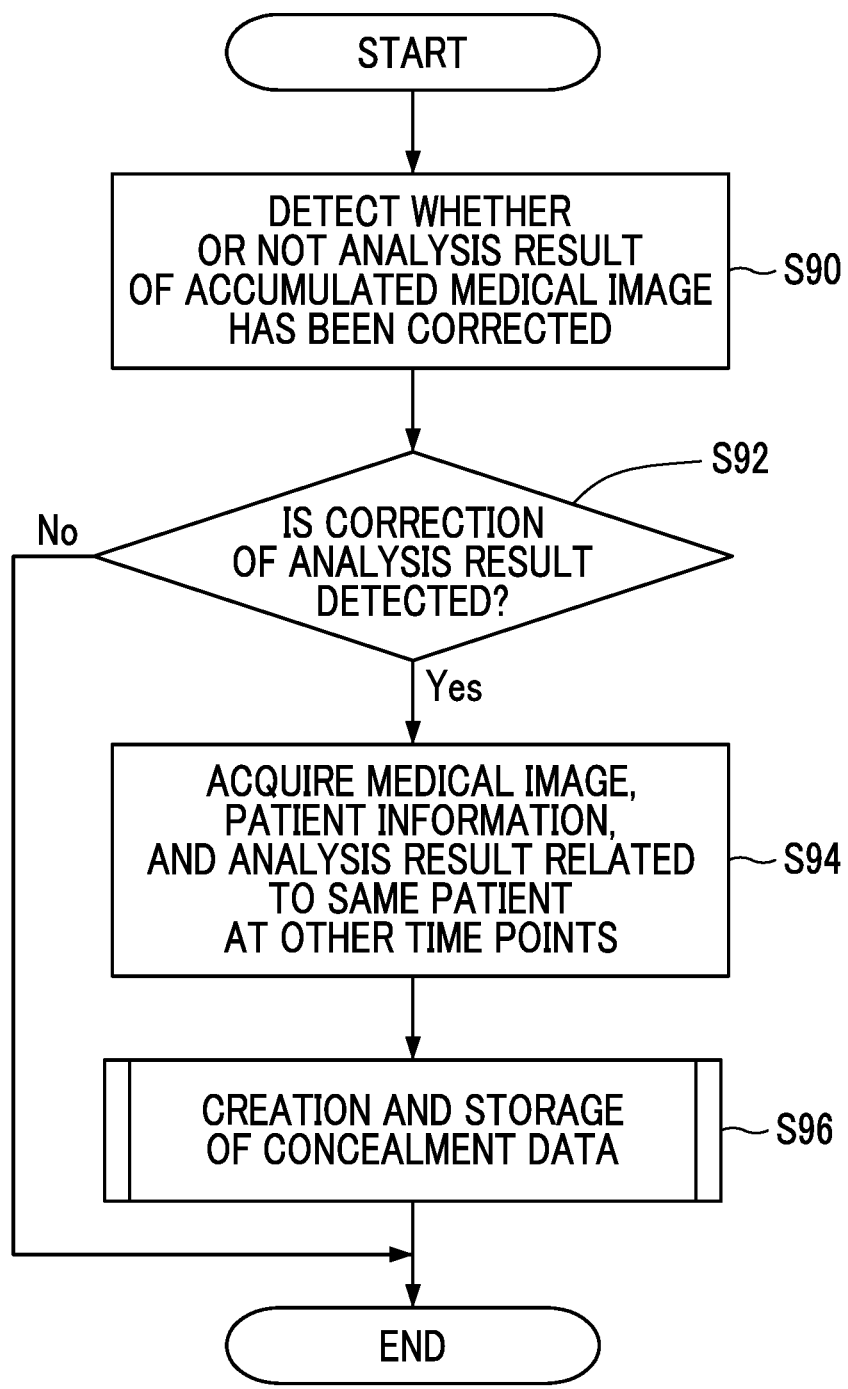
FIG. 15 is a flowchart illustrating a modification example of the medical image processing method according to the third embodiment of the present invention.

Next, a modification example of the processing in FIG. 14 will be described with reference to FIG. 15. FIG. 15 is a flowchart illustrating a modification example of the medical image processing method according to the third embodiment of the present invention.

First, the detection unit 116 detects, from the DICOM file F2 accumulated in the recording unit 108, those in which the analysis result of the medical image IMG1 has been corrected in the diagnosis support apparatus 200-*i* (step S90). Then, in a case where the DICOM file F2 in which the analysis result has been corrected is not detected (No in step S92), the processing ends.

On the other hand, in a case where the DICOM file F2 (a first time point) in which the analysis result has been corrected is detected (Yes in step S92), the data processing unit 118 reads out the patient identification information from the DICOM file F2 detected in step S90. Then, the data processing unit 118 acquires, from the recording unit 108, the DICOM file F2 related to the same patient, which is a second time point different from the first time point as in step S78 on the basis of the patient identification information (step S94).

Next, the data processing unit 118 performs the concealment processing on the past DICOM file F2 acquired in step S94 in addition to the DICOM file F2 acquired in step S90 to create the concealment data DCi, and stores the concealment data DCi in the concealment data storage unit 120 (step S96).

According to the present embodiment, in a case where the analysis result of the medical image IMG1 is corrected, it is possible to perform the concealment processing on a medical image of the same patient at another time point. This makes it possible to perform additional learning using analysis results of the medical image related to the same patient at multiple time points.

Fourth Embodiment

Figure 16:
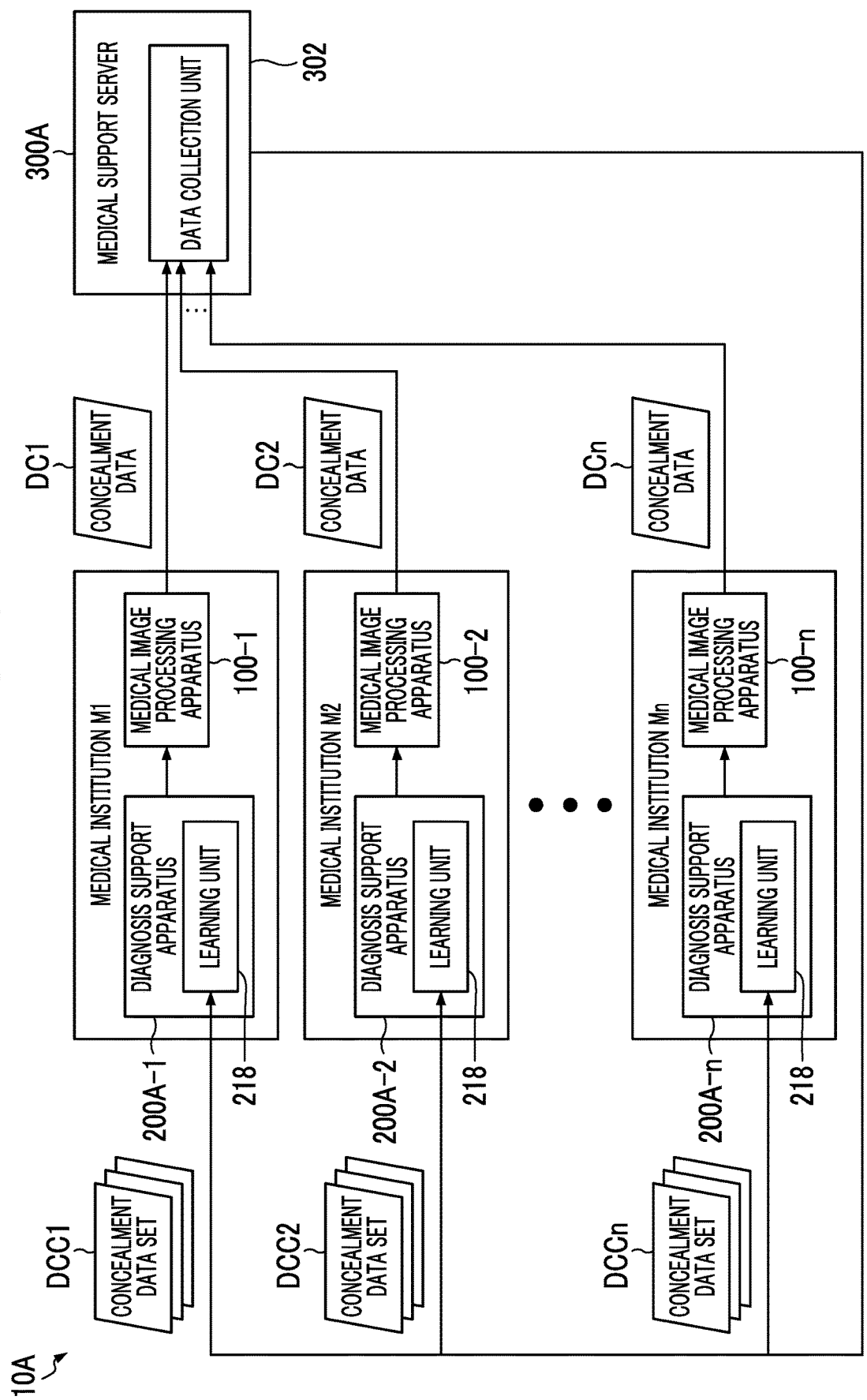
FIG. 16 is a block diagram illustrating a medical support system according to a fourth embodiment of the present invention.
Figure 17:
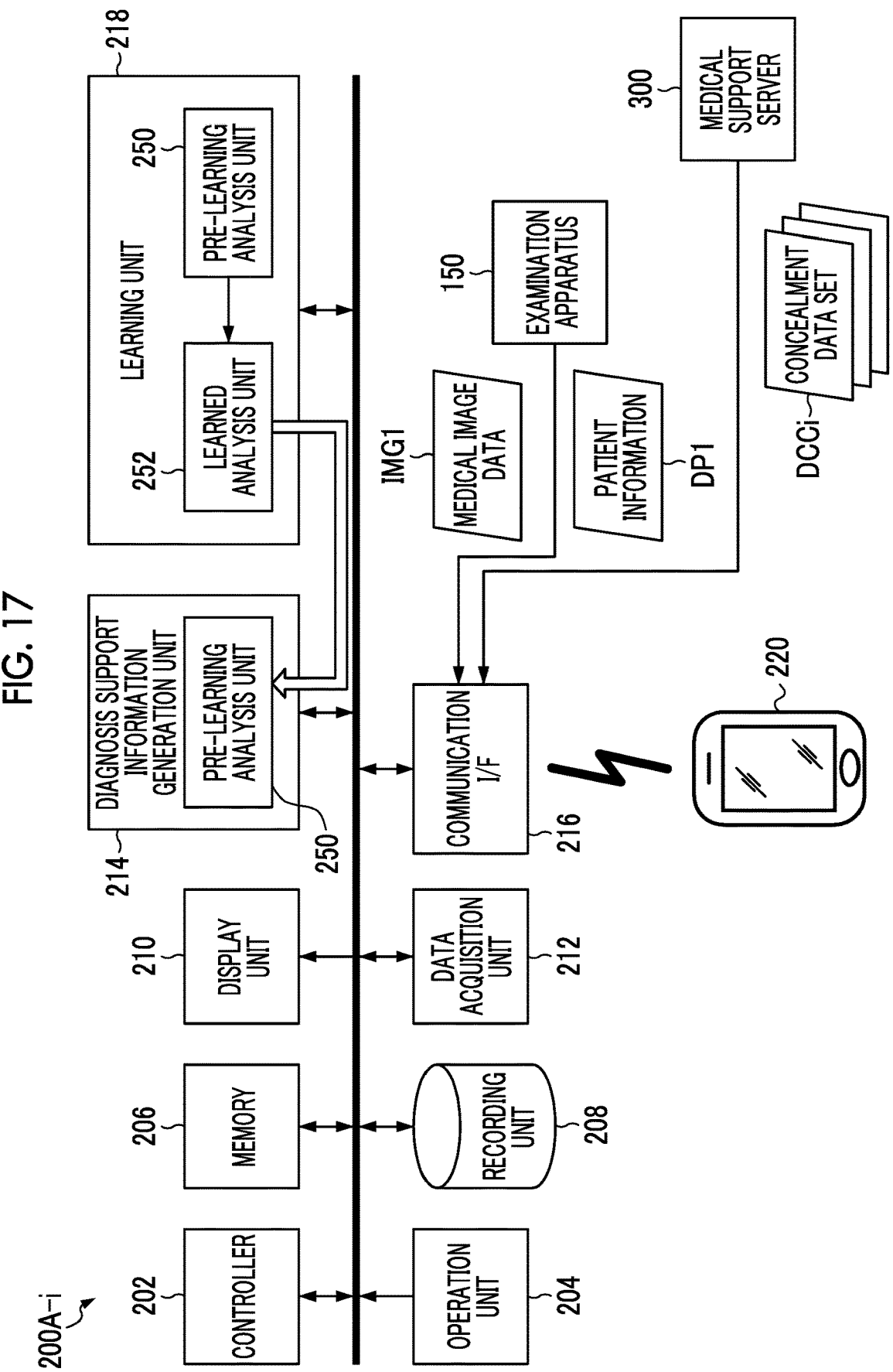
FIG. 17 is a block diagram illustrating a diagnosis support apparatus according to the fourth embodiment of the present invention.
Figure 18:
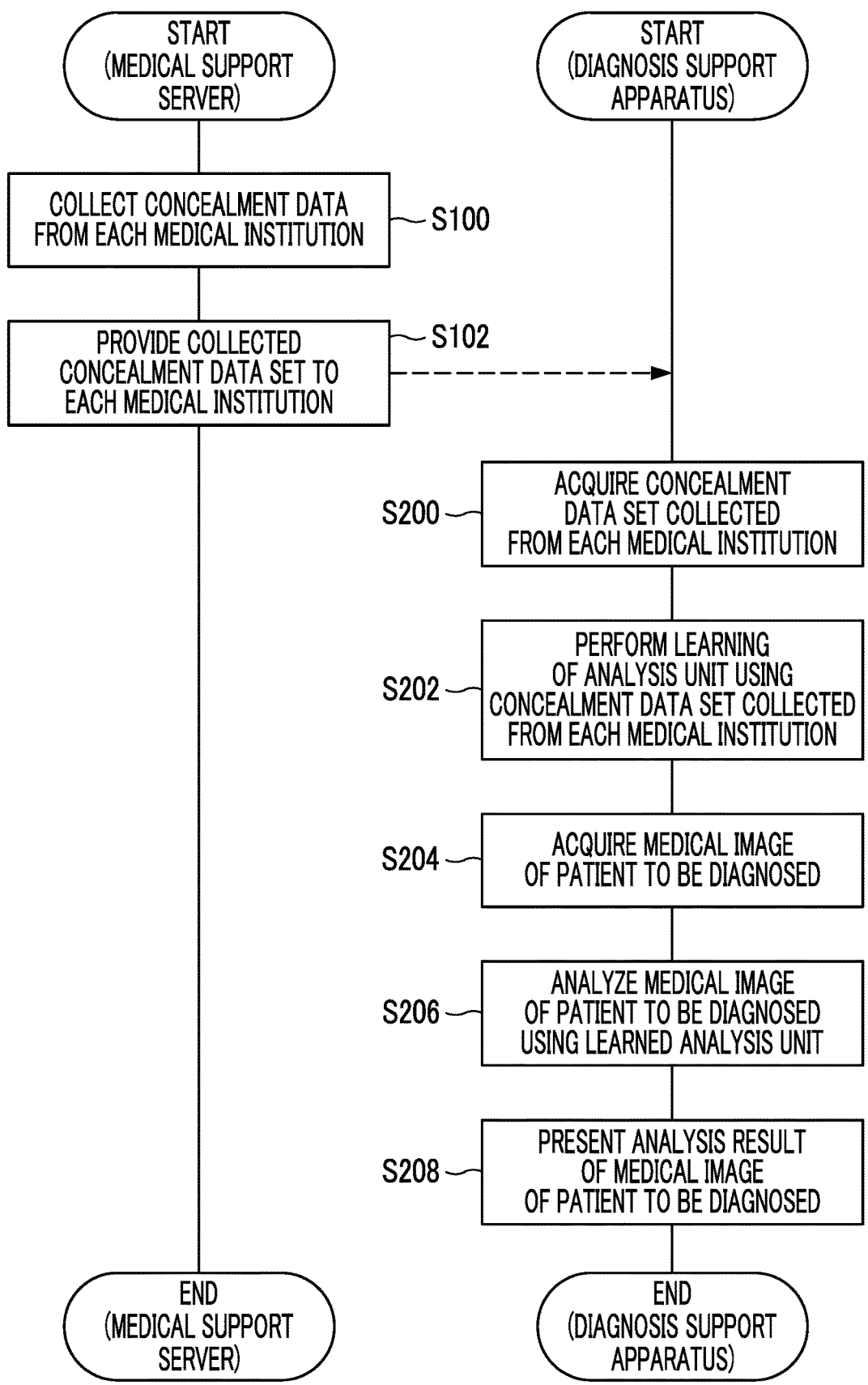
FIG. 18 is a flowchart illustrating a flow of processing in a diagnosis support method according to the fourth embodiment of the present invention.

Next, a fourth embodiment of the present invention will be described with reference to FIGS. 16 to 18. While the first to third embodiments are configured to perform learning of the medical image identification engine in the medical support server 300, the fourth embodiment is configured to perform learning of the medical image identification engine in the medical institution Mi side.

First, the medical support system according to the present embodiment will be described with reference to FIGS. 16 and 17. FIG. 16 is a block diagram illustrating a medical support system according to the fourth embodiment of the present invention. FIG. 17 is a block diagram illustrating a diagnosis support apparatus according to the fourth embodiment of the present invention.

In a medical support system 10A according to the present embodiment, a medical support server 300A collects the concealment data DCi from the medical institution Mi. The concealment data DCi is accumulated by the medical support server 300A to generate a set of concealment data (a concealment data set DCCi). The concealment data set DCCi is transmitted from the medical support server 300A to each medical institution Mi.

The concealment data set DCCi may include all the concealment data DC1, DC2, . . . , DCn collected from the medical institutions M1, M2, . . . , Mn. The concealment data set DCCi may be the concealment data DC1, DC2, . . . , DCn excluding the concealment data DCi of the medical institution Mi which is a transmission destination.

The diagnosis support apparatus 200A-i according to the present embodiment further comprises a learning unit 218 in addition to the configuration described in the first embodiment.

The learning unit 218 causes a pre-learning analysis unit 250 to perform learning using the concealment data set DCCi acquired from the medical support server 300A, as in the first embodiment. In addition, in a case where it is the concealment data DC1, DC2, . . . , DCn excluding the concealment data DCi of the medical institution Mi which is the transmission destination, the concealment data set DCCi performs learning using the concealment data DCi in addition to the concealment data set DCCi. Thereby, the learned analysis unit 252 is generated. The diagnosis support information generation unit 214 updates the medical image identification engine by acquiring the learned analysis unit 252 from the learning unit 218 and replacing it with the pre-learning analysis unit 250.

Since the medical image processing apparatus and method according to the present embodiment are the same as those in the first to third embodiments, descriptions thereof will be omitted.

Next, the diagnosis support method according to the present embodiment will be described with reference to FIG. 18. FIG. 18 is a flowchart illustrating a flow of processing in a diagnosis support method according to the fourth embodiment of the present invention.

First, in the medical support server 300A, the data collection unit 302 collects the concealment data DC1, DC2, . . . , DCn respectively from the medical institutions M1, M2, . . . , Mn (step S100). The concealment data DC1, DC2, . . . , DCn collected from the medical institutions M1, M2, . . . , Mn are accumulated in the medical support server 300A to generate the concealment data sets DCC1, DCC2, . . . , DCCn for each of the medical institutions M1, M2, . . . , Mn. The concealment data sets DCC1, DCC2, . . . , DCCn are provided to the medical institutions M1, M2, . . . , Mn (step S102).

Next, the diagnosis support apparatus 200A-i acquires the concealment data set DCCi from the medical support server 300A via the communication I/F 216 (step S200).

The learning unit 218 of the diagnosis support apparatus 200A-i causes the medical image identification engine (the pre-learning analysis unit 250) to perform learning using the concealment data set DCCi acquired from the medical support server 300A (step S202). The diagnosis support information generation unit 214 updates the medical image identification engine by replacing the learned analysis unit 252 with the pre-learning analysis unit 350.

Next, in a case where the data acquisition unit 212 of the diagnosis support apparatus 200A-i acquires a medical image of a patient to be diagnosed from the examination apparatus 150 (step S204), the diagnosis support information generation unit 214 analyzes the medical image of the patient to be diagnosed using the learned analysis unit 352 (step S206). Then, the diagnosis support information generation unit 214 causes the display unit 210 to display the analysis result of the medical image of the patient to be diagnosed as the diagnosis support information DA0 (step S208).

In the fourth embodiment, the diagnosis support apparatus 200A-i of the medical institution Mi acquires the concealment data DCi provided from the medical image processing apparatus 100-i of another medical institution via the medical support server 300A, but the present invention is not limited to thereto. For example, a peer to peer (P2P) type network may be formed by the medical image processing apparatus 100-i and the diagnosis support apparatus 200A-i of the medical institution Mi, and the diagnosis support apparatus 200A-i of the medical institution Mi may directly acquire the concealment data DCi from the medical image processing apparatus 100-i of another medical institution.

[About Invention of Program]

The present invention can also be realized as a program (a medical image processing program and a diagnosis support program) for causing a computer to realize the above processing, or a non-transitory recording medium or a program product housing such a program. By applying such a program to a computer, it becomes possible for arithmetic unit, a recording unit, and the like of the computer to realize a function corresponding to each step of the method according to the present embodiment.

In each of the embodiments, for example, in the medical image processing apparatus 100-i, the diagnosis support apparatuses 200-i and 200A-i, and the medical support servers 300 and 300A, a hardware structure of a processing unit that executes various types of processing can be realized as the following various types of processors. The various processors include a central processing unit (CPU) as a general-purpose processor functioning as various processing units by executing software (program), a programmable logic device (PLD) as a processor of which the circuit configuration can be changed after manufacturing such as a field programmable gate array (FPGA), and a dedicated electric circuit which is a processor having a circuit configuration specifically designed to execute specific processing such as an application specific integrated circuit (ASIC).

One processing unit may be configured with one of these various processors, or may be configured with two or more same kind or different kinds of processors (for example, a plurality of FPGAs, or a combination of a CPU and an FPGA). Further, a plurality of processing units may be formed of one processor. As an example where a plurality of processing units is configured with one processor, first, there is an aspect where one processor is configured with a combination of one or more CPUs and software as typified by a computer, such as a client or a server, and functions as a plurality of processing units. Second, as represented by a system on chip (SoC), there is an aspect in which a processor that realizes the functions of the entire system including the plurality of processing units by one integrated circuit (IC) chip is used. In this way, various processing units are formed using one or more of the above-mentioned various processors as hardware structures.

In addition, the hardware structures of these various processors are more specifically electrical circuitry where circuit elements such as semiconductor elements, are combined.

EXPLANATION OF REFERENCES 10, 10A: medical support system
M1, M2, ..., Mn: medical institutions
100-1, 100-2, ..., 100-n: medical image processing apparatus
102: controller
104: operation unit
106: memory
108: recording unit
110: display unit
112: medical image reception unit
114: analysis result acquisition unit
116: detection unit
118: data processing unit
120: concealment data storage unit
122: communication I/F
150: examination apparatus
200-1, 200-2, ..., 200-n, 200A-1, 200A-2, ..., 200A-n: diagnosis support apparatus
202: controller
204: operation unit
206: memory
208: recording unit
210: display unit
212: data acquisition unit
214: diagnosis support information generation unit
216: communication I/F
218: learning unit
220: physician terminal
250: pre-learning analysis unit
252: learned analysis unit
300, 300A: medical support server
302: data collection unit
304: learning unit
350: pre-learning analysis unit
352: learned analysis unit
DP1: patient information
DP2: concealed patient information
DA0: diagnosis support information
DA1: analysis result information
DA2: concealed analysis result information
DC1, DC2, ..., DCn: concealment data
DCC1, DCC2, ..., DCCn: concealment data set
F1, F2: DICOM file
IMG1: medical image
IMG2: concealed medical image
S10 to S18, S70 to S80, S90 to S96: each step of medical image processing method
S30 to S34, S50 to S54, S100, S102, S200 to S208: each step of diagnosis support method
S180 to S184: each step of creation and storage of concealment data

What is claimed is:

1. A medical image processing apparatus comprising:
a storage medium; and
a processor coupled to the storage medium and configured to:
receive an input of a medical image and patient information corresponding to the medical image;
acquire an analysis result obtained by analyzing the medical image;
detect whether or not the analysis result has been corrected; and
create and store, in the storage medium, data in which identification information capable of identifying a patient is concealed in a case where it is detected that the analysis result has been corrected,
wherein the processor is further configured to record in advance a correspondence relationship between a type of the medical image or a type of the analysis and a level of concealment of the identification information, and create the data in which the identification information capable of identifying the patient is concealed on the basis of the correspondence relationship.

2. The medical image processing apparatus according to claim 1, wherein the processor is configured to detect that the analysis result has been corrected by comparing the analysis result with an input for the analysis result or a medical examination record of the patient.

3. The medical image processing apparatus according to claim 1, wherein, in the case where it is detected that the analysis result has been corrected, the processor is configured to create and store, in the storage medium, data in which the identification information capable of identifying the patient is concealed on the basis of the medical image, the patient information, and the corrected analysis result.

4. The medical image processing apparatus according to claim 1, wherein, in a case where the processor has detected that an extraction result of a contour of a region included in the medical image has been corrected, the processor is configured to create and store, in the storage medium, the data in which the identification information capable of identifying the patient is concealed on the basis of the medical image and the corrected contour.

5. The medical image processing apparatus according to claim 1, wherein, in a case where the processor has detected that a determination result of a property of a region included in the medical image has been corrected, the processor is configured to create and store, in the storage medium, the data in which the identification information capable of identifying the patient is concealed on the basis of the medical image and the corrected determination result.

6. The medical image processing apparatus according to claim 1, wherein, in a case where the processor has detected that an analysis result including one or more keywords or sentences obtained by an image analysis for the medical image has been corrected, the processor is configured to create and store, in the storage medium, the data in which the identification information capable of identifying the patient is concealed on the basis of the medical image and the corrected analysis result including one or more keywords or sentences.

7. The medical image processing apparatus according to claim 1, wherein, in a case where the medical image includes an image of a body surface of the patient, the processor is configured to process the medical image and conceals the image of the body surface.

8. The medical image processing apparatus according to claim 1, wherein, in the case where it is detected that the analysis result has been corrected, the processor is configured to acquire a past medical image and patient information regarding the patient, and processor is configured to create and store, in the storage medium, data in which the identification information capable of identifying the patient is concealed, among the past medical image and patient information.

9. The medical image processing apparatus according to claim 1, wherein the processor is configured to detect whether or not at least one of a plurality of analysis results at different time points regarding the patient has been corrected, and wherein, in a case where it is detected that the analysis result at a first time point has been corrected, the processor is configured to acquire a medical image and patient information at a second time point different from the first time point in addition to a medical image and patient information at the first time point, and processor is configured to create and store, in the storage medium, data in which the identification information capable of identifying the patient is concealed, in the medical image and the patient information.

10. A diagnosis support apparatus that presents information for supporting a diagnosis, comprising:
a controller configured to:
acquire a medical image of a patient to be diagnosed;
perform learning using data created by the medical image processing apparatus according to claim 1, and analyze the medical image of the patient to be diagnosed; and
a display panel that presents an analysis result.

11. A medical image processing method performed in a medical image processing apparatus, the method comprising:
receiving an input of a medical image and patient information corresponding to the medical image;
acquiring an analysis result obtained by analyzing the medical image;
detecting whether or not the analysis result has been corrected;
creating and storing data in which identification information capable of identifying a patient is concealed in a case where it is detected that the analysis result has been corrected;
recording in advance a correspondence relationship between a type of the medical image or a type of the analysis and a level of concealment of the identification information; and
creating the data in which the identification information capable of identifying the patient is concealed on the basis of the correspondence relationship.

12. A diagnosis support method comprising:
performing learning in an analysis unit for analyzing a medical image using data created by the medical image processing method according to claim 11;
acquiring a medical image of a patient to be diagnosed;
analyzing the medical image of the patient to be diagnosed by the analysis unit that has performed the learning; and
presenting an analysis result.

13. A non-transitory, computer-readable recording medium which records therein, computer instructions that, when executed by a computer, causes the computer to realize:
receiving an input of a medical image and patient information corresponding to the medical image;
acquiring an analysis result obtained by analyzing the medical image;
detecting whether or not the analysis result has been corrected;
creating and storing data in which identification information capable of identifying a patient is concealed in a case where it is detected that the analysis result has been corrected;
recording in advance a correspondence relationship between a type of the medical image or a type of the analysis and a level of concealment of the identification information; and
creating the data in which the identification information capable of identifying the patient is concealed on the basis of the correspondence relationship.

14. A non-transitory, computer-readable recording medium which records therein, computer instructions that, when executed by a computer, causes the computer to realize:

performing learning in an analysis unit for analyzing a medical image using data created by reading and executing the computer instructions recorded in the recording medium according to claim 13;

acquiring a medical image of a patient to be diagnosed;

analyzing the medical image of the patient to be diagnosed by the analysis unit that has performed the learning; and presenting an analysis result.

* * * * *